(12) United States Patent
Cabrera

(10) Patent No.: US 8,968,329 B2
(45) Date of Patent: Mar. 3, 2015

(54) SURGICAL RETRIEVAL APPARATUS FOR THORACIC PROCEDURES

(71) Applicant: Covidien LP, Mansfield, MA (US)

(72) Inventor: Ramiro Cabrera, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 209 days.

(21) Appl. No.: 13/649,305

(22) Filed: Oct. 11, 2012

(65) Prior Publication Data
US 2013/0103043 A1    Apr. 25, 2013

Related U.S. Application Data

(60) Provisional application No. 61/549,015, filed on Oct. 19, 2011.

(51) Int. Cl.
| | |
|---|---|
| A61B 17/22 | (2006.01) |
| A61B 17/00 | (2006.01) |
| A61B 17/02 | (2006.01) |
| A61B 17/29 | (2006.01) |

(52) U.S. Cl.
CPC ....... *A61B 17/00234* (2013.01); *A61B 17/0293* (2013.01); *A61B 2017/00287* (2013.01); *A61B 2017/2927* (2013.01)
USPC ............ 606/127; 606/113; 606/114; 606/128

(58) Field of Classification Search
CPC ................. A61B 17/22; A61B 17/221; A61B 2017/2212; A61B 2017/2215; A61B 2017/2927; A61B 2017/00287; A61B 2017/2217; A61B 17/00234; A61B 17/0293
USPC .................. 606/113, 114, 127, 128
See application file for complete search history.

(56) References Cited

U.S. PATENT DOCUMENTS

| | | |
|---|---|---|
| 30,471 A | 10/1860 | Dudley |
| 35,164 A | 5/1862 | Logan et al. |
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |

(Continued)

FOREIGN PATENT DOCUMENTS

| | | |
|---|---|---|
| DE | 3542667 A1 | 6/1986 |
| DE | 8435489 U1 | 8/1986 |
| DE | 4204210 A1 | 8/1992 |
| DE | 19624826 A1 | 1/1998 |
| EP | 2184014 A2 | 5/2010 |
| FR | 1272412 A | 9/1961 |
| WO | 9315675 A1 | 8/1993 |
| WO | 9509666 A1 | 4/1995 |
| WO | 2004002334 A1 | 1/2004 |
| WO | 2005112783 A1 | 12/2005 |

OTHER PUBLICATIONS

EP Search Report for EP 12158873 mailed Jul. 19, 2012.

*Primary Examiner* — Tuan V Nguyen
*Assistant Examiner* — Christian Knauss

(57) ABSTRACT

A surgical retrieval apparatus includes a handle including an elongated sleeve extending therefrom that, together cooperate to define a lumen therethrough. A shaft having an end effector assembly disposed at a distal end thereof and a plunger disposed at a proximal end thereof is selectively translatable between a first position and a second position, wherein the end effector assembly extends from the sleeve. An articulation mechanism is configured to articulate the end effector assembly relative to the shaft. A specimen retrieval bag is coupled to the end effector assembly and is deployable to an extended position upon movement of the end effector assembly to the second position.

12 Claims, 26 Drawing Sheets

(56) References Cited

U.S. PATENT DOCUMENTS

| | | | | |
|---|---|---|---|---|
| 4,744,363 | A | 5/1988 | Hasson | |
| 4,790,812 | A | 12/1988 | Hawkins, Jr. et al. | |
| 4,927,427 | A | 5/1990 | Kriauciunas et al. | |
| 4,997,435 | A | 3/1991 | Demeter | |
| 5,037,379 | A | 8/1991 | Clayman et al. | |
| 5,074,867 | A | 12/1991 | Wilk | |
| 5,084,054 | A | 1/1992 | Bencini et al. | |
| 5,143,082 | A | 9/1992 | Kindberg et al. | |
| 5,147,371 | A * | 9/1992 | Washington et al. | 606/127 |
| 5,176,687 | A | 1/1993 | Hasson et al. | |
| 5,190,542 | A | 3/1993 | Nakao et al. | |
| 5,190,555 | A * | 3/1993 | Wetter et al. | 606/114 |
| 5,190,561 | A | 3/1993 | Graber | |
| 5,192,286 | A | 3/1993 | Phan et al. | |
| 5,201,740 | A | 4/1993 | Nakao et al. | |
| 5,215,521 | A | 6/1993 | Cochran et al. | |
| 5,224,930 | A | 7/1993 | Spaeth et al. | |
| 5,234,439 | A | 8/1993 | Wilk et al. | |
| 5,279,539 | A | 1/1994 | Bohan et al. | |
| 5,312,416 | A * | 5/1994 | Spaeth et al. | 606/114 |
| 5,330,483 | A | 7/1994 | Heaven et al. | |
| 5,336,227 | A | 8/1994 | Nakao et al. | |
| 5,337,754 | A | 8/1994 | Heaven et al. | |
| 5,341,815 | A | 8/1994 | Cofone et al. | |
| 5,352,184 | A * | 10/1994 | Goldberg et al. | 600/37 |
| 5,354,303 | A * | 10/1994 | Spaeth et al. | 606/128 |
| 5,368,545 | A | 11/1994 | Schaller et al. | |
| 5,368,597 | A | 11/1994 | Pagedas | |
| 5,370,647 | A * | 12/1994 | Graber et al. | 606/127 |
| 5,405,360 | A * | 4/1995 | Tovey | 606/151 |
| 5,465,731 | A | 11/1995 | Bell et al. | |
| 5,480,404 | A * | 1/1996 | Kammerer et al. | 606/113 |
| 5,486,182 | A | 1/1996 | Nakao et al. | |
| 5,486,183 | A * | 1/1996 | Middleman et al. | 606/127 |
| 5,499,988 | A | 3/1996 | Espiner et al. | |
| 5,524,633 | A * | 6/1996 | Heaven et al. | 600/562 |
| 5,535,759 | A | 7/1996 | Wilk | |
| 5,601,572 | A * | 2/1997 | Middleman et al. | 606/139 |
| 5,611,803 | A | 3/1997 | Heaven et al. | |
| 5,618,296 | A | 4/1997 | Sorensen et al. | |
| 5,630,822 | A | 5/1997 | Hermann et al. | |
| 5,642,282 | A | 6/1997 | Sonehara | |
| 5,643,282 | A | 7/1997 | Kieturakis | |
| 5,643,283 | A | 7/1997 | Younker | |
| 5,645,083 | A | 7/1997 | Essig et al. | |
| 5,647,372 | A * | 7/1997 | Tovey et al. | 600/562 |
| 5,649,902 | A | 7/1997 | Yoon | |
| 5,658,296 | A | 8/1997 | Bates et al. | |
| 5,679,423 | A | 10/1997 | Shah | |
| 5,720,754 | A * | 2/1998 | Middleman et al. | 606/127 |
| 5,735,289 | A * | 4/1998 | Pfeffer et al. | 600/564 |
| 5,755,724 | A | 5/1998 | Yoon | |
| 5,759,187 | A | 6/1998 | Nakao et al. | |
| 5,769,794 | A | 6/1998 | Conlan et al. | |
| 5,779,716 | A * | 7/1998 | Cano et al. | 606/114 |
| 5,785,677 | A | 7/1998 | Auweiler | |
| 5,788,709 | A | 8/1998 | Riek et al. | |
| 5,792,145 | A | 8/1998 | Bates et al. | |
| 5,814,044 | A | 9/1998 | Hooven | |
| 5,836,953 | A | 11/1998 | Yoon | |
| 5,853,374 | A | 12/1998 | Hart et al. | |
| 5,895,392 | A | 4/1999 | Riek et al. | |
| 5,906,621 | A | 5/1999 | Secrest et al. | |
| 5,957,884 | A | 9/1999 | Hooven | |
| 5,971,995 | A | 10/1999 | Rousseau | |
| 5,980,544 | A | 11/1999 | Vaitekunas | |
| 5,997,547 | A | 12/1999 | Nakao et al. | |
| 6,004,330 | A | 12/1999 | Middleman et al. | |
| 6,007,512 | A | 12/1999 | Hooven | |
| 6,019,770 | A | 2/2000 | Christoudias | |
| 6,036,681 | A | 3/2000 | Hooven | |
| 6,059,793 | A | 5/2000 | Pagedas | |
| 6,123,701 | A | 9/2000 | Nezhat | |
| 6,152,932 | A | 11/2000 | Ternstrom | |
| 6,162,235 | A | 12/2000 | Vaitekunas | |
| 6,165,121 | A | 12/2000 | Alferness | |
| 6,168,603 | B1 | 1/2001 | Leslie et al. | |
| 6,228,095 | B1 | 5/2001 | Dennis | |
| 6,270,505 | B1 | 8/2001 | Yoshida et al. | |
| 6,277,083 | B1 | 8/2001 | Eggers et al. | |
| 6,280,450 | B1 | 8/2001 | McGuckin, Jr. | |
| 6,344,026 | B1 | 2/2002 | Burbank et al. | |
| 6,348,056 | B1 | 2/2002 | Bates et al. | |
| 6,350,266 | B1 | 2/2002 | White et al. | |
| 6,350,267 | B1 | 2/2002 | Stefanchik | |
| 6,383,195 | B1 * | 5/2002 | Richard | 606/114 |
| 6,383,196 | B1 | 5/2002 | Leslie et al. | |
| 6,383,197 | B1 * | 5/2002 | Conlon et al. | 606/114 |
| 6,387,102 | B2 * | 5/2002 | Pagedas | 606/127 |
| 6,406,440 | B1 | 6/2002 | Stefanchik | |
| 6,409,733 | B1 * | 6/2002 | Conlon et al. | 606/114 |
| 6,419,639 | B2 | 7/2002 | Walther et al. | |
| 6,447,523 | B1 * | 9/2002 | Middleman et al. | 606/127 |
| 6,471,659 | B2 | 10/2002 | Eggers et al. | |
| 6,506,166 | B1 | 1/2003 | Hendler et al. | |
| 6,508,773 | B2 | 1/2003 | Burbank et al. | |
| 6,589,252 | B2 | 7/2003 | McGuckin, Jr. | |
| 6,752,811 | B2 | 6/2004 | Chu et al. | |
| 6,755,779 | B2 | 6/2004 | Vanden Hoek et al. | |
| 6,780,193 | B2 | 8/2004 | Leslie et al. | |
| 6,805,699 | B2 * | 10/2004 | Shimm | 606/200 |
| 6,840,948 | B2 | 1/2005 | Albrecht et al. | |
| 6,872,211 | B2 | 3/2005 | White et al. | |
| 6,887,255 | B2 | 5/2005 | Shimm | |
| 6,994,696 | B2 | 2/2006 | Suga | |
| 7,052,454 | B2 | 5/2006 | Taylor | |
| 7,052,501 | B2 | 5/2006 | McGuckin, Jr. | |
| 7,090,637 | B2 | 8/2006 | Danitz et al. | |
| 7,270,663 | B2 | 9/2007 | Nakao | |
| 7,273,488 | B2 | 9/2007 | Nakamura et al. | |
| 7,410,491 | B2 | 8/2008 | Hopkins et al. | |
| 7,547,310 | B2 | 6/2009 | Whitfield | |
| 7,621,923 | B2 * | 11/2009 | Goldenberg | 606/127 |
| 2004/0097960 | A1 | 5/2004 | Terachi et al. | |
| 2004/0133213 | A1 * | 7/2004 | Bagley et al. | 606/127 |
| 2004/0138587 | A1 | 7/2004 | Lyons | |
| 2004/0243173 | A1 * | 12/2004 | Inoue | 606/200 |
| 2005/0267492 | A1 * | 12/2005 | Poncet et al. | 606/114 |
| 2006/0052799 | A1 | 3/2006 | Middleman et al. | |
| 2006/0058776 | A1 | 3/2006 | Bilsbury | |
| 2006/0200169 | A1 | 9/2006 | Sniffin | |
| 2006/0200170 | A1 | 9/2006 | Aranyi | |
| 2006/0212040 | A1 * | 9/2006 | Goldstein | 606/107 |
| 2006/0229639 | A1 | 10/2006 | Whitfield | |
| 2006/0229640 | A1 * | 10/2006 | Whitfield | 606/114 |
| 2006/0293697 | A1 * | 12/2006 | Nakao et al. | 606/127 |
| 2007/0016224 | A1 | 1/2007 | Nakao | |
| 2007/0016225 | A1 | 1/2007 | Nakao | |
| 2007/0073251 | A1 | 3/2007 | Zhou et al. | |
| 2007/0088370 | A1 * | 4/2007 | Kahle et al. | 606/114 |
| 2007/0106304 | A1 * | 5/2007 | Hammack et al. | 606/113 |
| 2007/0135780 | A1 | 6/2007 | Pagedas | |
| 2007/0135781 | A1 | 6/2007 | Hart | |
| 2008/0091215 | A1 * | 4/2008 | Saleh | 606/113 |
| 2008/0188766 | A1 | 8/2008 | Gertner | |
| 2008/0221588 | A1 * | 9/2008 | Hollis et al. | 606/114 |
| 2008/0234696 | A1 * | 9/2008 | Taylor et al. | 606/114 |
| 2008/0300621 | A1 | 12/2008 | Hopkins et al. | |
| 2008/0312496 | A1 | 12/2008 | Zwolinski | |
| 2009/0082779 | A1 * | 3/2009 | Nakao | 606/114 |
| 2009/0182292 | A1 | 7/2009 | Egle et al. | |
| 2009/0192510 | A1 | 7/2009 | Bahney | |
| 2009/0240238 | A1 | 9/2009 | Grodrian et al. | |
| 2009/0306683 | A1 * | 12/2009 | Zwolinski et al. | 606/144 |
| 2010/0000471 | A1 | 1/2010 | Hibbard | |
| 2010/0152746 | A1 * | 6/2010 | Ceniccola et al. | 606/114 |
| 2011/0184311 | A1 * | 7/2011 | Parihar et al. | 600/562 |
| 2011/0184430 | A1 * | 7/2011 | Parihar et al. | 606/114 |

(56) References Cited

U.S. PATENT DOCUMENTS

| | | |
|---|---|---|
| 2011/0184431 A1* | 7/2011 | Parihar et al. ............ 606/114 |
| 2011/0184432 A1* | 7/2011 | Parihar et al. ............ 606/114 |
| 2011/0184433 A1* | 7/2011 | Parihar et al. ............ 606/114 |
| 2011/0184434 A1* | 7/2011 | Parihar et al. ............ 606/114 |
| 2011/0184435 A1* | 7/2011 | Parihar et al. ............ 606/114 |
| 2011/0184436 A1* | 7/2011 | Shelton et al. ............ 606/114 |
| 2011/0190781 A1 | 8/2011 | Collier et al. |
| 2011/0299799 A1 | 12/2011 | Towe |

* cited by examiner

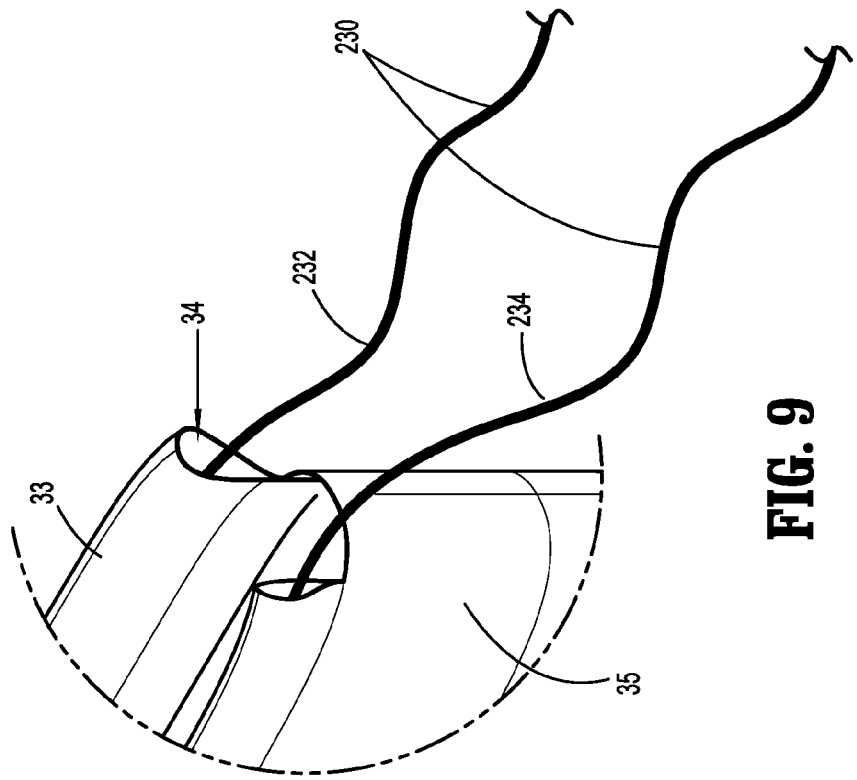
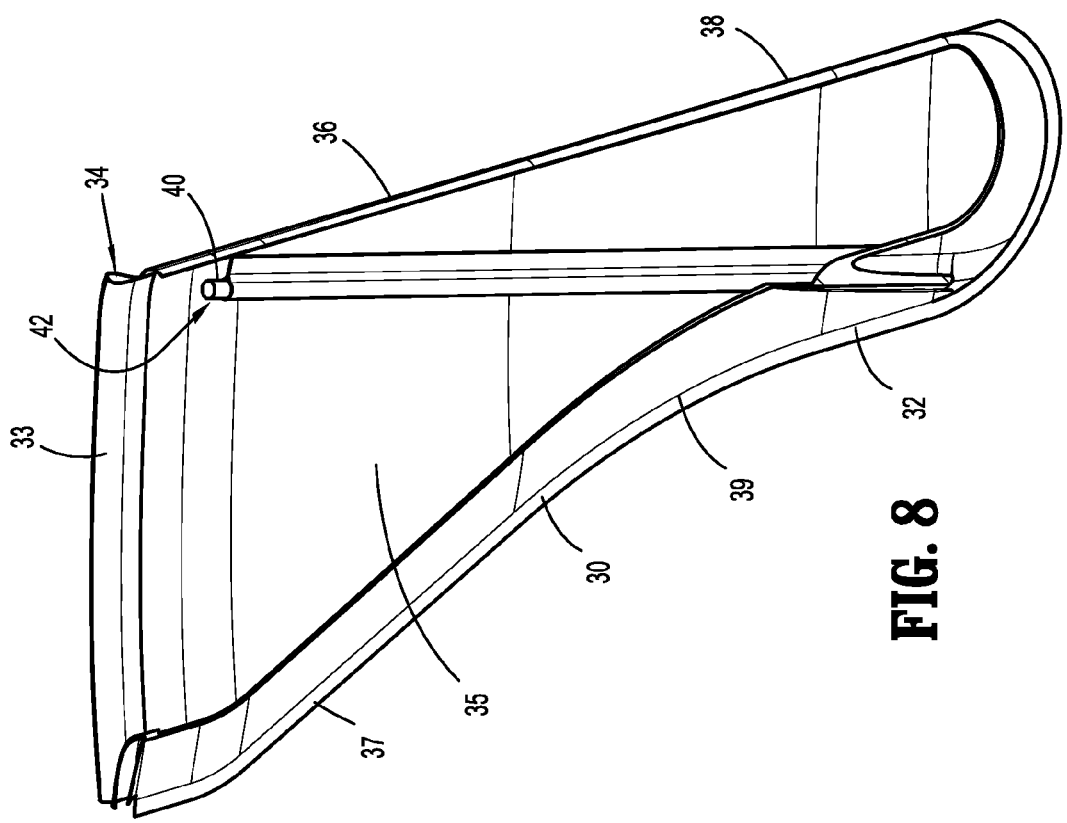
FIG. 9
FIG. 8

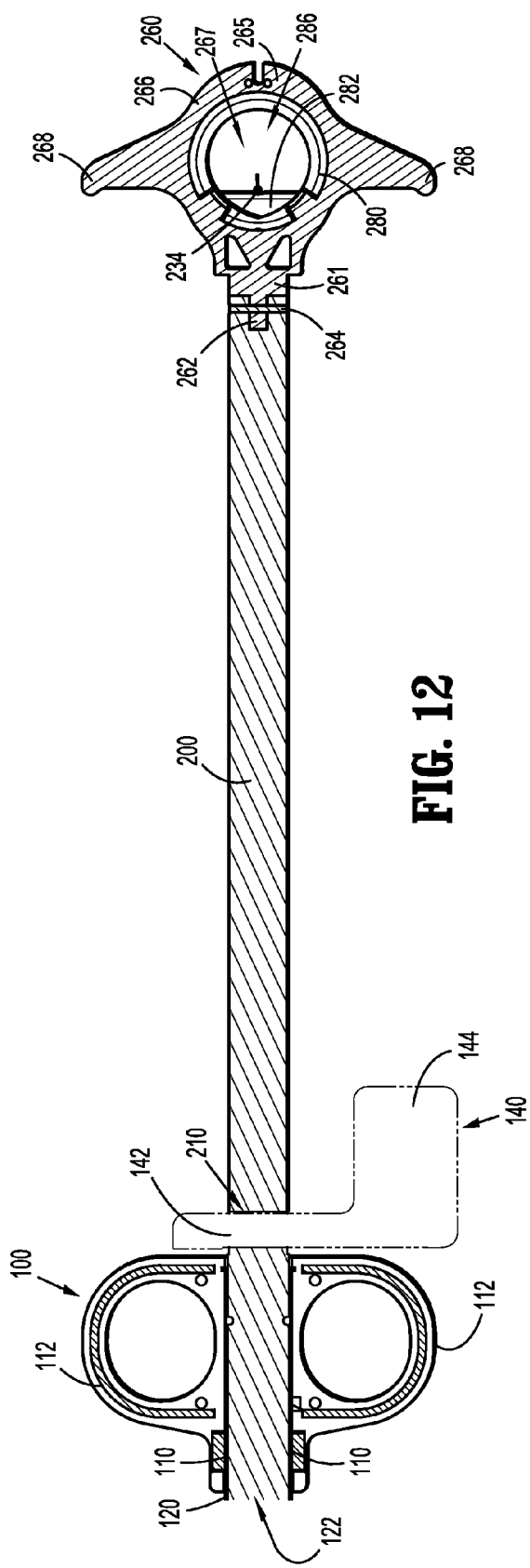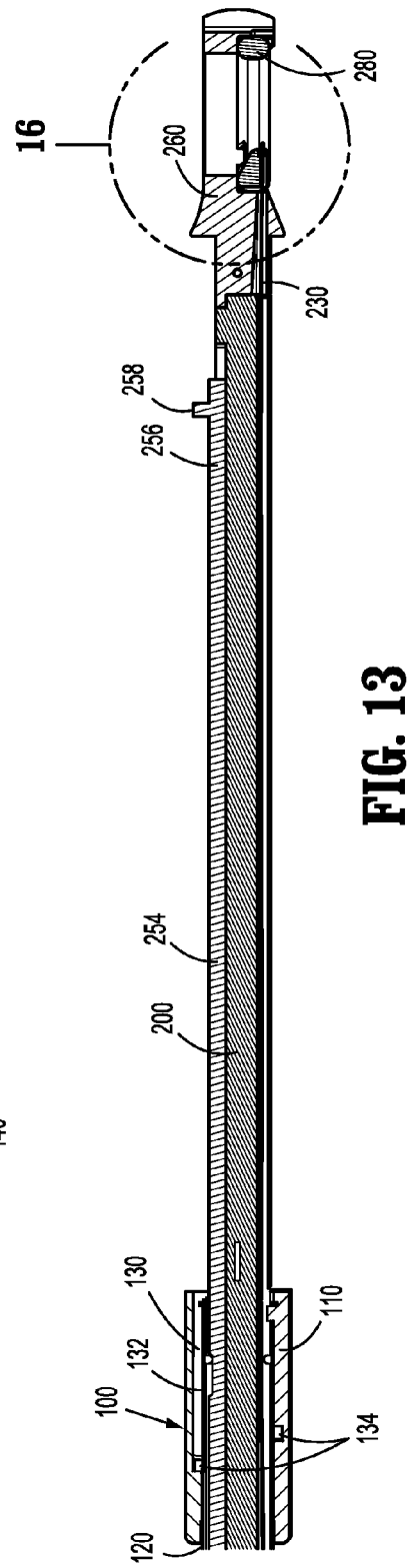

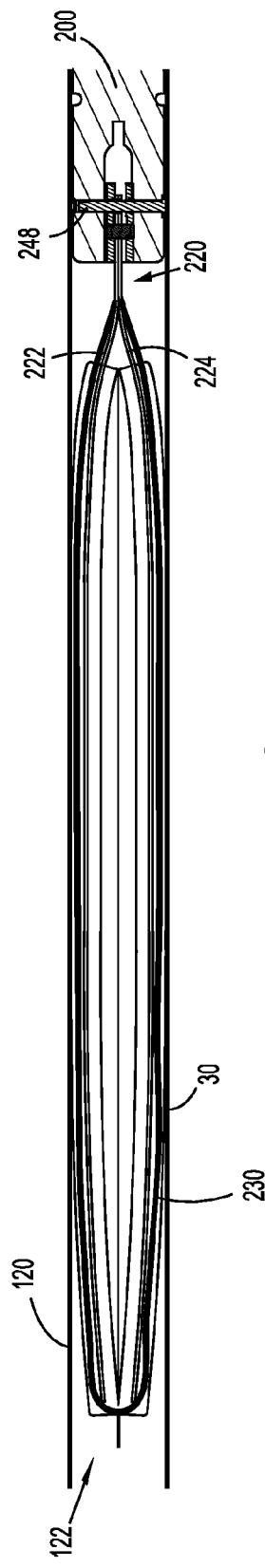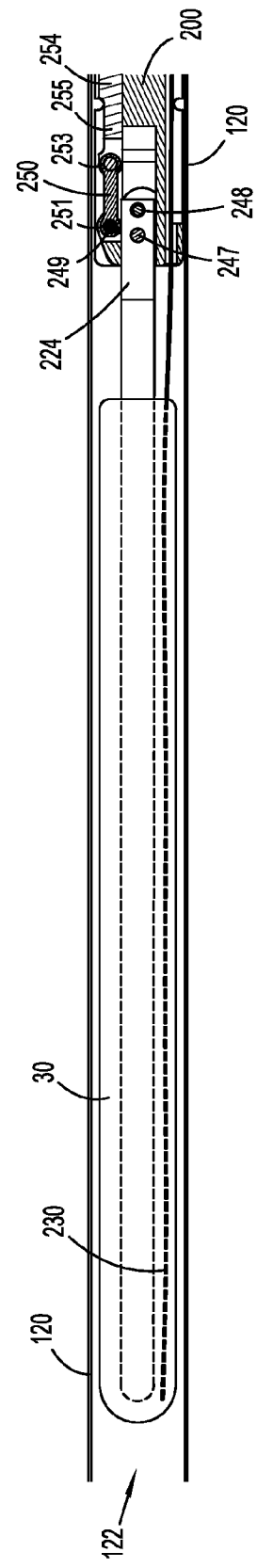

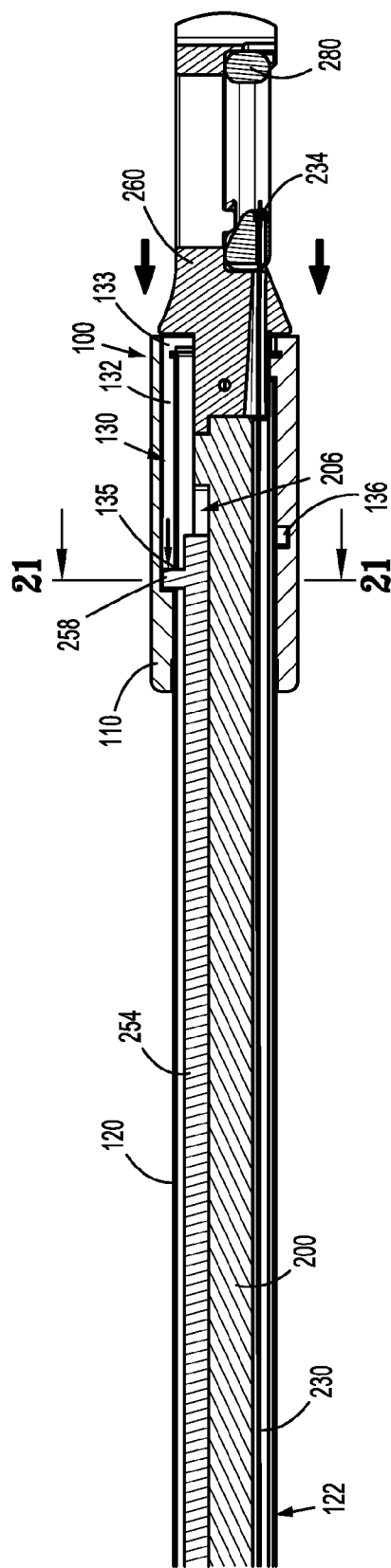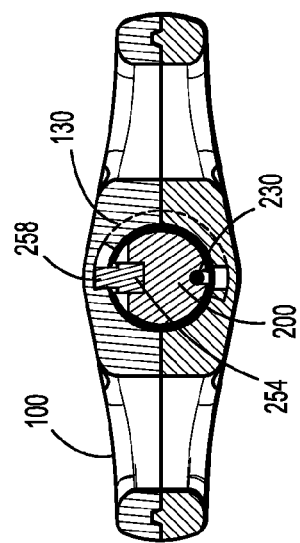
FIG. 20
FIG. 21

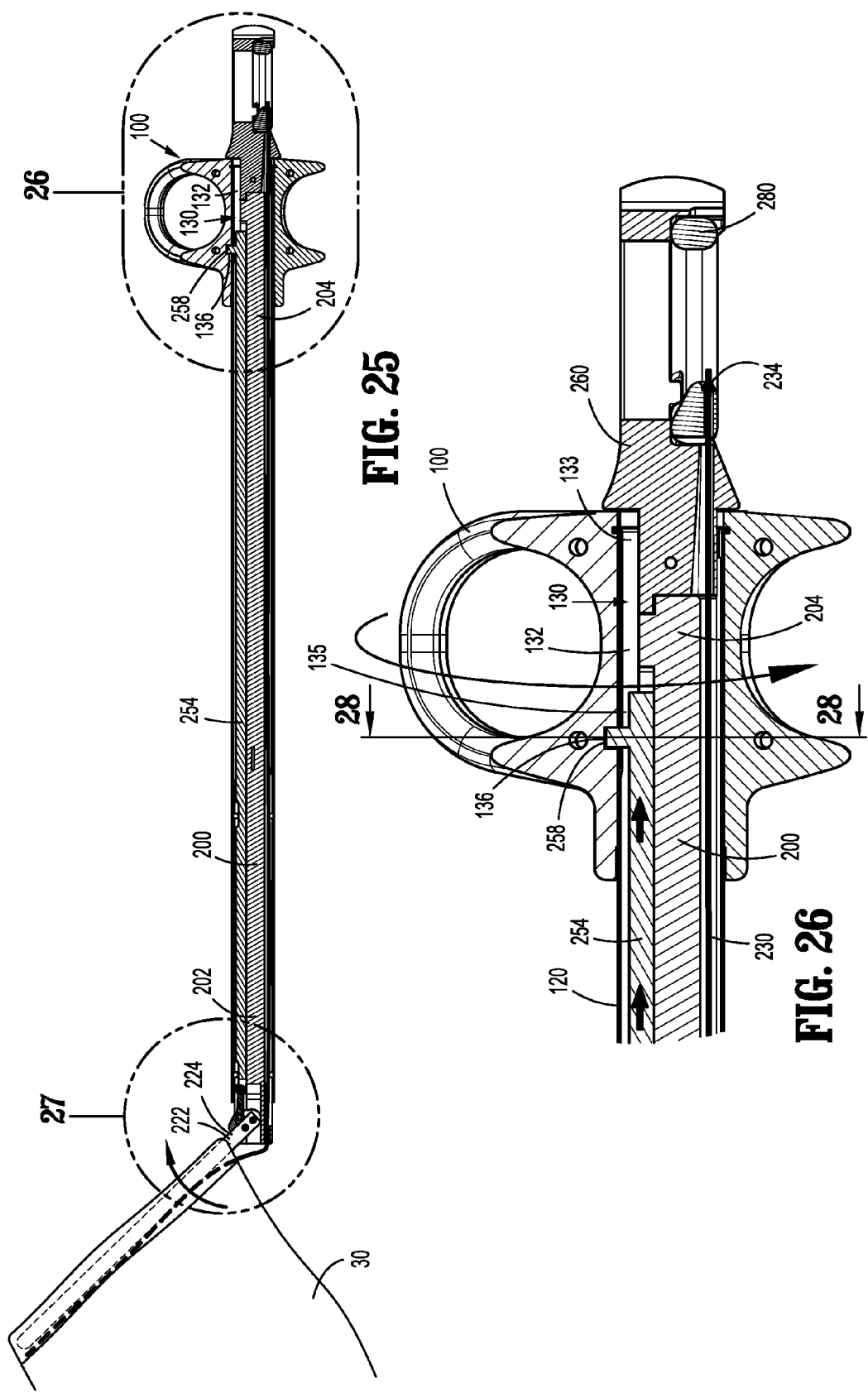

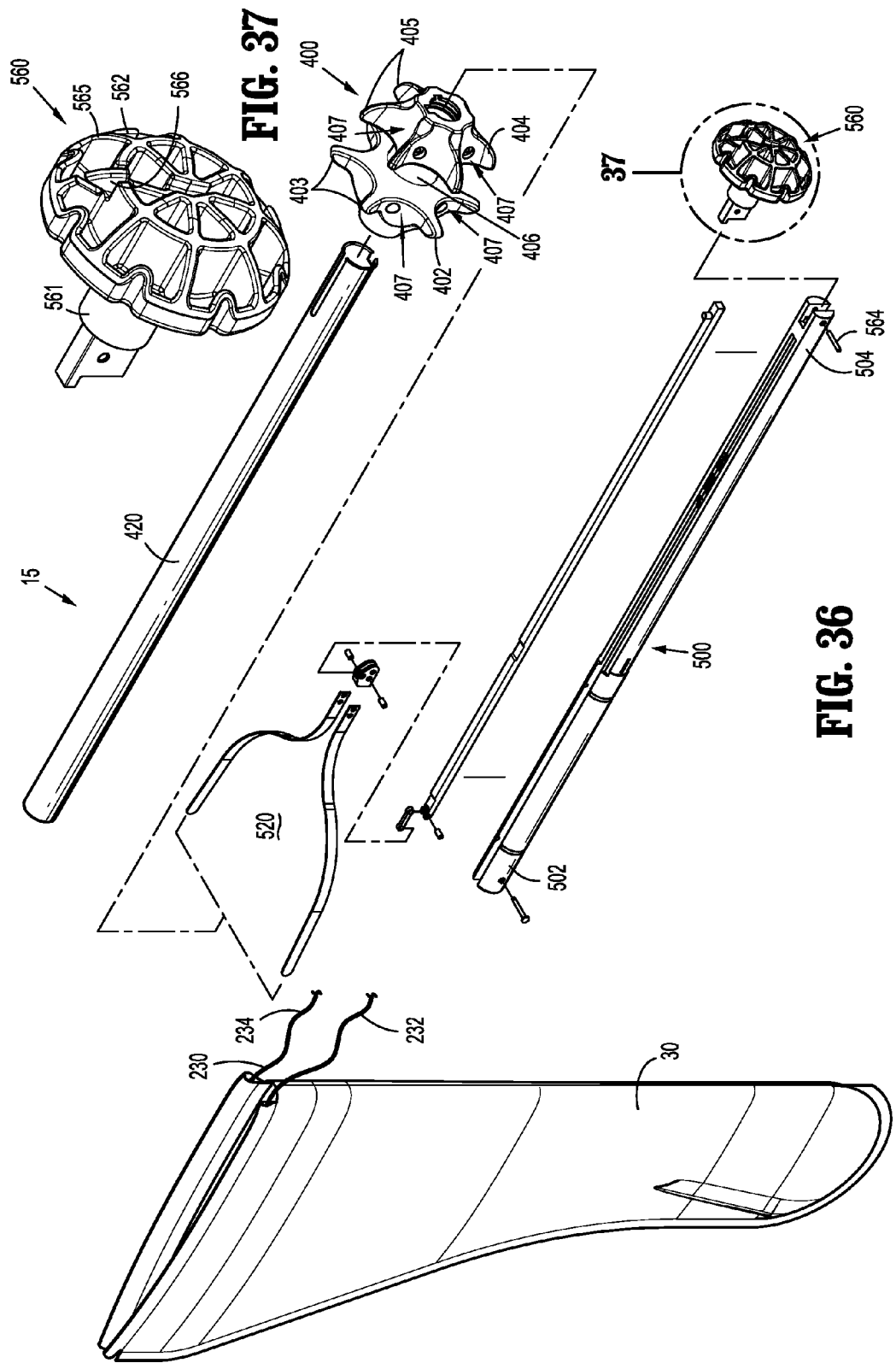

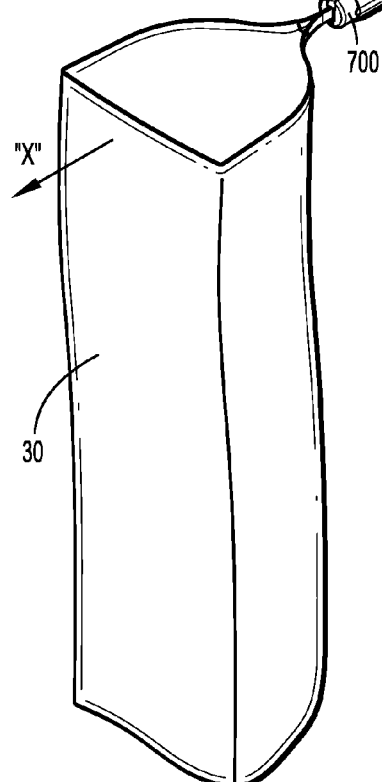
FIG. 38
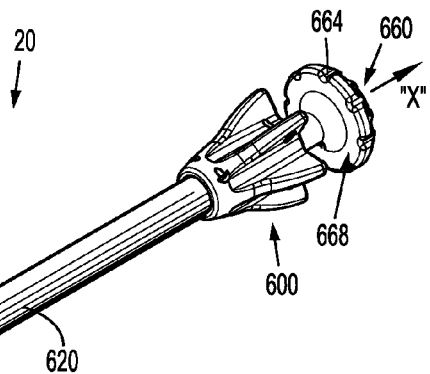
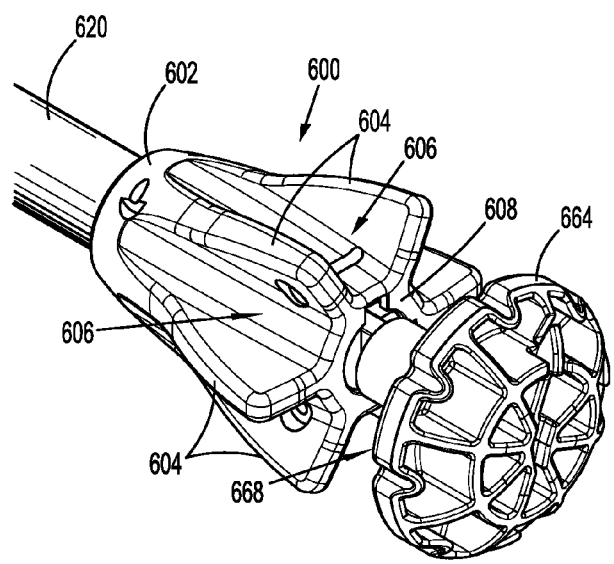
FIG. 39

SURGICAL RETRIEVAL APPARATUS FOR THORACIC PROCEDURES

CROSS REFERENCE TO RELATED APPLICATION

The present application claims the benefit of and priority to U.S. Provisional Application Ser. No. 61/549,015, filed on Oct. 19, 2011, the entire contents of which are incorporated herein by reference.

BACKGROUND

1. Technical Field

The present disclosure relates to a retrieval apparatus, and more particularly, to a surgical retrieval apparatus for use in thoracic surgical procedures.

2. Background of Related Art

In minimally invasive surgical procedures, operations are carried out within the body by using elongated instruments inserted through small entrance openings in the body. The initial opening in the body tissue to allow passage of instruments to the interior of the body may be a natural passageway of the body, or it can be created by a tissue piercing instrument such as a trocar, or created by a small incision into which a cannula is inserted.

Because the tubes, instrumentation, and any required punctures or incisions are relatively small, the surgery is less invasive as compared to conventional surgical procedures in which the surgeon is required to cut open large areas of body tissue. Therefore, minimally invasive surgery minimizes trauma to the patient and reduces patient recovery time and hospital costs.

Minimally invasive procedures may be used for partial or total removal of body tissue or organs from the interior of the body, e.g. nephrectomy, cholecystectomy, lobectomy and other procedures including thoracic, laparoscopic and endoscopic procedures. During such procedures, it is common that a cyst, tumor, or other affected tissue or organ needs to be removed via the access opening in the skin, or through a cannula. Various types of entrapment devices have been disclosed to facilitate this procedure. In many procedures where cancerous tumors are removed, removal of the specimen in an enclosed environment is highly desirable to inhibit seeding of cancer cells.

In minimally invasive thoracic surgery, access to the thoracic cavity is limited as well as maneuverability within the cavity as the access port is placed between the confined space between a patient's ribs. Such procedures, commonly referred to as video assisted thoracoscopic surgery (VATS), aim to reduce patient recovery time by accessing the thoracic cavity through the natural intercostal space without spreading the ribs as in open procedures. This restricted access can sometimes cause problems when removing large specimens. Moreover, in such procedures, e.g. thorascopic wedge resection and lobectomy, it is often necessary to remove a portion of the lung and retrieve it relatively intact for pathology. It is also important that the specimen be sufficiently contained to inhibit seeding of cancer cells during manipulation and removal.

In designing such specimen retrieval instrumentation, a balance must be struck between the need to provide a retrieval apparatus with a strong enough containment bag to inhibit tearing or rupture while providing sufficient rigidity to enable manipulation and removal. Another balance which needs to be achieved is to provide sufficient maneuverability while reducing tissue trauma, e.g. damaging lung tissue, during manipulation and removal. Additionally, the instrumentation on one hand should be able to be inserted through a small access incision or port while on the other hand able to accommodate a wide range of patient sizes and be able to easily remove large specimens and minimize risk of seeding.

SUMMARY

In accordance with embodiments of the present disclosure, a surgical retrieval apparatus is provided. The surgical retrieval apparatus includes a handle defining a longitudinal axis and an elongated sleeve extending distally therefrom. The handle and the elongated sleeve cooperate to define a lumen extending longitudinally therethrough. A shaft having an end effector assembly disposed at a distal end thereof and a plunger disposed at a proximal end thereof is also provided. The shaft is selectively translatable through the lumen between a first position, and a second position, wherein the end effector assembly extends distally from the elongated sleeve. An articulation mechanism configured to articulate the end effector assembly relative to the shaft between a substantially aligned position and an articulated position is also provided. The handle is rotatable about the longitudinal axis and relative to the shaft to articulate the end effector assembly. A specimen retrieval bag is coupled, and preferably releasably coupled, to the end effector assembly and is configured to be deployable from an undeployed position to an extended position upon movement of the end effector assembly from the first position to the second position. The specimen retrieval bag further includes a cinch cord disposed about an open end thereof.

In some embodiments, the cinch cord is removably coupled to the plunger at an end thereof and is configured, upon release from the plunger, for selective proximal translation to cinch closed the specimen retrieval bag.

In some embodiments, articulation of the end effector assembly is inhibited when the shaft is disposed in the first position.

In some embodiments, the handle may define an articulation track on an inner surface thereof. The articulation track may be configured to receive an articulation post of the articulation mechanism therein such that the articulation post is translated along the track upon rotation of the handle assembly about the longitudinal axis and relative to the shaft to articulate the end effector assembly. Further, the articulation mechanism may include an articulation bar coupled to the end effector assembly at a distal end thereof and the articulation post disposed at a proximal end thereof. The articulation bar is disposed within the shaft and be translatable relative to the shaft upon rotation of the handle assembly relative to the shaft to articulate the end effector assembly relative to the shaft In some embodiments, the shaft is manually translatable between the first and second positions. The handle may include one or more finger holes to facilitate manipulation of the handle.

In some embodiments, a safety tab is configured to engage both the handle and the shaft when the shaft is disposed in the first position. The safety tab inhibits relative movement between the handle and the shaft.

In some embodiments, a pull-member is releasably coupled to the plunger and configured to engage the end of the cinch cord thereon such that, upon release from the plunger, the pull-member is translatable proximally to cinch closed the specimen retrieval bag. Further, the plunger may include one or more resilient lock tabs configured to releasably engage the pull-member thereon. The plunger may also include one or more flanges extending outwardly therefrom that are configured to facilitate translation of the shaft between the first and second positions.

In some embodiments, translation of the shaft from the second position back to the first position separates the specimen retrieval bag from the end effector assembly and/or at least partially cinches closed the specimen retrieval bag.

A method of specimen retrieval using the specimen retrieval apparatus of any of the above-embodiments is also provided in accordance with the present disclosure. The method includes positioning the surgical retrieval apparatus within an internal body cavity, translating the shaft distally through the lumen from a first position to a second position such that the end effector assembly extends distally from the elongated sleeve to deploy the specimen retrieval bag, articulating the end effector assembly relative to the shaft from a substantially aligned position to an articulated position by rotating the handle about the longitudinal axis relative to the shaft, positioning a specimen of tissue within the specimen retrieval bag, articulating the end effector assembly back to the substantially aligned position, translating the shaft proximally from the second position back to the first position such that the end effector assembly is disposed within the elongated sleeve, disengaging the cinch cord from the plunger, and translating the cinch cord proximally to cinch closed the specimen retrieval bag about the specimen of tissue.

In some embodiments, the method further includes cutting the cinch cord to release the specimen retrieval bag from the shaft. Thereafter, the cut end of the cinch cord may be translated proximally to remove the specimen retrieval bag from the internal body cavity.

In some embodiments, prior to positioning the surgical retrieval apparatus within the internal body cavity, a safety tab coupled to both the handle and the shaft is removed to permit translation of the shaft relative to the handle.

BRIEF DESCRIPTION OF THE DRAWINGS

Various embodiments of the subject surgical retrieval apparatus are described herein with reference to the drawings wherein:

FIG. 8 is a side, cut-away view of a specimen retrieval bag configured for use with the surgical retrieval apparatus of FIG. 1;

FIG. 9 is an enlarged, perspective view of a proximal end of the specimen retrieval bag of FIG. 8;

FIG. 12 is an enlarged, top, longitudinal cross-sectional view of a proximal end of the surgical retrieval apparatus of FIG. 1, shown in the retracted position;

FIG. 13 is an enlarged, side, longitudinal cross-sectional view of the area of detail designated in FIG. 10 showing the distal end of the surgical retrieval apparatus of FIG. 1, in the retracted position;

FIG. 14 is an enlarged, top, longitudinal cross-sectional view of a distal end of the surgical retrieval apparatus of FIG. 1, shown in the retracted position;

FIG. 15 is an enlarged, side, longitudinal cross-sectional view of the area of detail designated in FIG. 10 showing the distal end of the surgical retrieval apparatus of FIG. 1, in the retracted position;

FIG. 20 is an enlarged, side, longitudinal cross-sectional view of the proximal end of the surgical retrieval apparatus of FIG. 1, shown in the deployed position;

FIG. 21 is a transverse, cross-sectional view of the proximal end of the surgical retrieval apparatus of FIG. 1 taken along line 21-21 of FIG. 20, shown in the deployed position;

FIG. 25 is a longitudinal cross-sectional view of the surgical retrieval apparatus of FIG. 1, shown in the articulated position;

FIG. 26 is a enlarged, longitudinal cross-sectional view of the area of detail of FIG. 25 showing the proximal end of the surgical retrieval apparatus of FIG. 1 in the articulated position;

FIG. 36 is an exploded, perspective view of the surgical retrieval apparatus of FIG. 35;

FIG. 37 is an enlarged, perspective view of a plunger of the surgical retrieval apparatus of FIG. 35;

FIG. 38 is a side, perspective view of yet another embodiment of a surgical retrieval apparatus provided in accordance with the present disclosure; and FIG. 39 is a perspective view of a proximal end of the surgical retrieval apparatus of FIG. 38.

DETAILED DESCRIPTION

Figure 1:
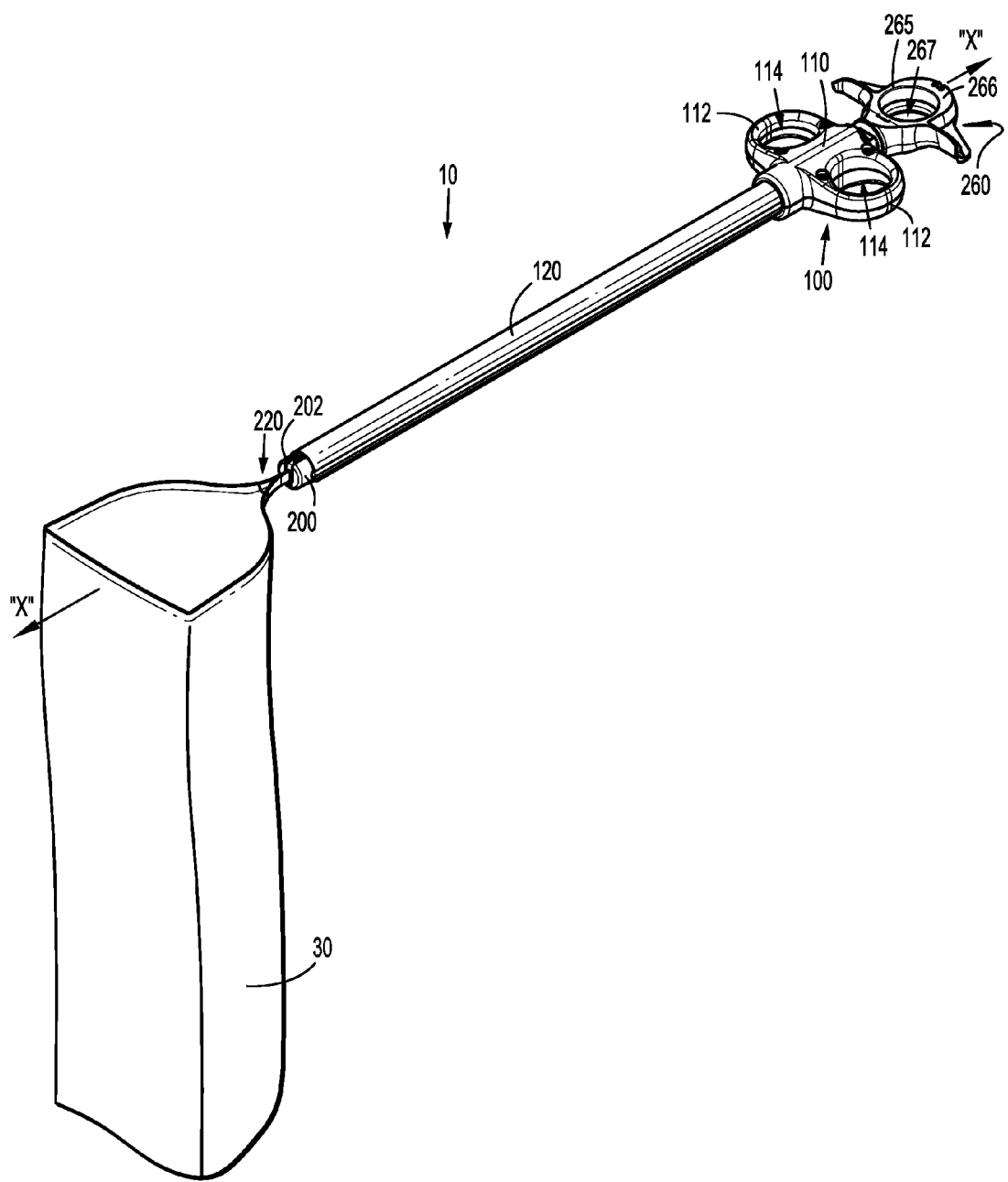
FIG. 1 is a side, perspective view of one embodiment of a surgical retrieval apparatus in accordance with the present disclosure, shown in a deployed (extended) position.

Various embodiments of the presently disclosed surgical retrieval apparatus, and methods of using the same, will now be described in detail with reference to the drawings wherein like references numerals identify similar or identical elements. In the drawings, and in the following description, the term "proximal" should be understood as referring to the end of the apparatus, or component thereof, that is closer to the clinician during proper use, while the term "distal" should be understood as referring to the end that is farther from the clinician, as is traditional and conventional in the art.

Although the presently disclosed surgical retrieval apparatus is discussed with respect to minimally invasive thoracic procedures, it is within the scope of the present disclosure that the surgical retrieval apparatus is readily adaptable for use in other minimally invasive surgical procedures.

Figure 2:
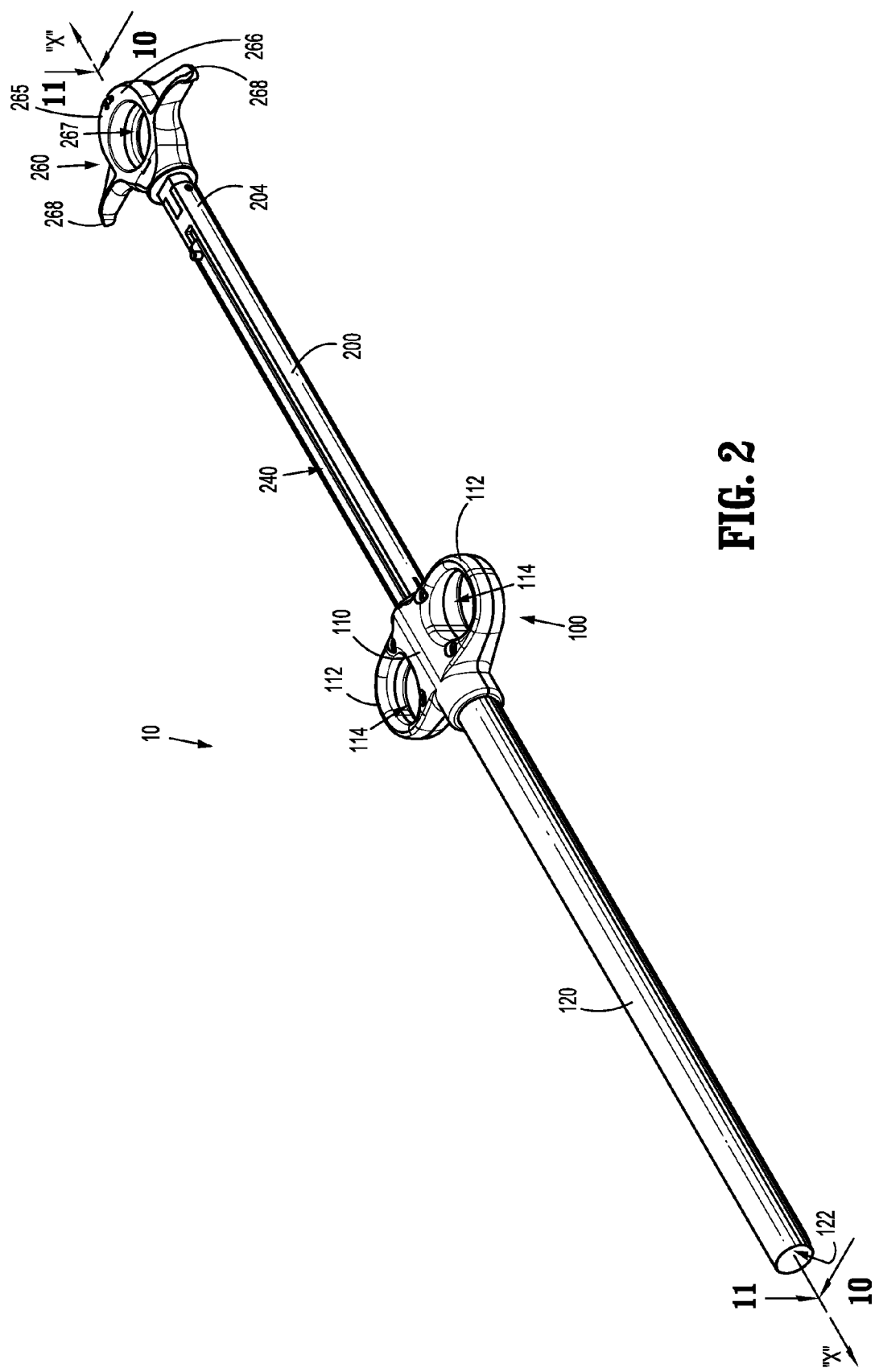
FIG. 2 is a side, perspective view of the surgical retrieval apparatus of FIG. 1, shown in a retracted (insertion/removal) position.
Figure 3:
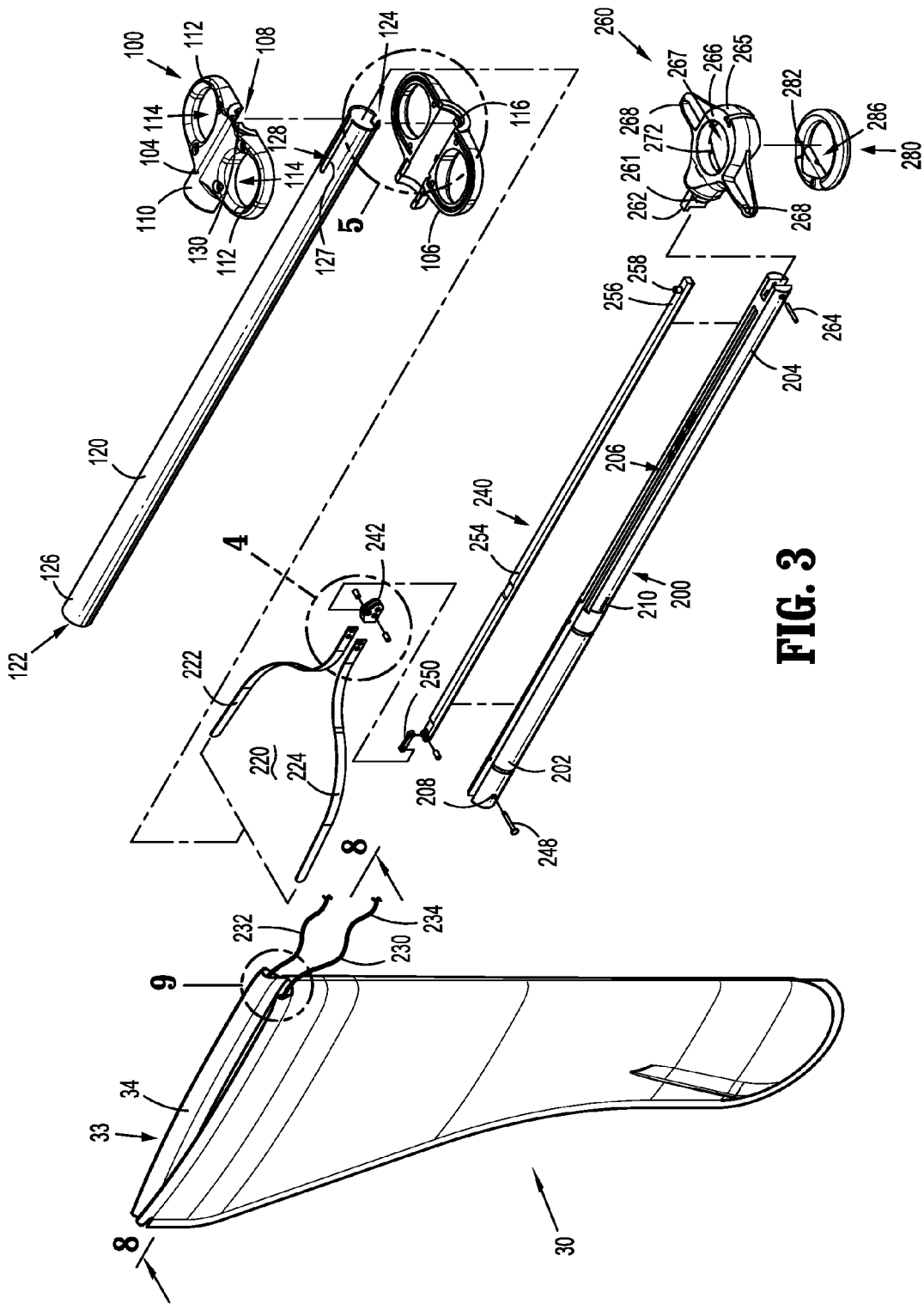
FIG. 3 is an exploded, perspective view of the surgical retrieval apparatus of FIG. 1.

Turning now to FIGS. 1-3, a surgical retrieval apparatus in accordance with the present disclosure is shown generally identified by reference numeral 10. Surgical retrieval apparatus 10 defines a longitudinal axis "X-X" and generally includes a handle 100 having an elongated sleeve 120 fixedly engaged thereto and extending distally therefrom, and a shaft 200 having an end effector assembly 220 disposed at a distal end 202 thereof, an articulation assembly 240 coupled thereto, and a plunger assembly 260 disposed at a proximal end 204 thereof. As will be described in detail below, shaft 200 and end effector assembly 220 are longitudinally translatable through and relative to handle 100 and elongated sleeve 120 to transition surgical retrieval apparatus 10 between a first, initial, insertion/removal, or retracted position (FIG. 2) and a second, extended, or deployed position (FIG. 1). Further, once the deployed position has been achieved, handle 100 may be rotated about longitudinal axis "X-X" and relative to shaft 200 to articulate end effector assembly 220 off of longitudinal axis "X-X," i.e., to define an acute angle between end effector assembly 220 and shaft 200.

Handle 100 is formed from a pair of cooperating housing components 104, 106, e.g., via snap-fitting, and includes a generally-cylindrical body portion 110 having a pair of opposed wings 112 extending outwardly therefrom. Each wing 112 includes a finger hole 114 defined therethrough that is configured to receive fingers of the clinician to facilitate grasping and/or manipulating surgical retrieval apparatus 10. As mentioned above, elongated sleeve 120 extends distally from handle 100. More specifically, elongated sleeve 120 includes one or more notches 124 defined therein that are configured to receive one or more complementary protrusions 116 of body portion 110 of handle 100 to fixedly secure elongated sleeve 120 within body portion 110 of handle 100 upon engagement between components 104, 106 of handle 100. Further, body portion 110 of handle 100 and elongated sleeve 120 together define a lumen 122 disposed about longitudinal axis "X-X" and extending distally from proximal aperture 108 of handle 100, through body portion 110 of handle 100, and through elongated sleeve 120 to distal end 126 thereof, i.e., lumen 122 extends completely through surgical retrieval apparatus 10 along longitudinal axis "X-X" thereof.

Elongated sleeve 120 is configured for insertion through an opening in tissue, e.g., through a thoracic surgical access portal 300 (FIGS. 18-19) disposed within an incision "I" (FIGS. 18-19) in tissue "T" (FIGS. 18-19) between adjacent ribs "R" (FIG. 19) of a patient. As such, it is envisioned that elongated sleeve 120 define a sufficient length such that elongated sleeve 120 may be advanced into the thoracic cavity "C" (FIG. 19) to a position adjacent a tissue specimen "S" (FIG. 29) to be removed, while handle 100 remains external of the patient. Further, it is envisioned that elongated sleeve 120 define a diameter sufficiently large to permit passage of end effector assembly 220 and shaft 200 therethrough, but sufficiently small such that elongated sleeve 120 may be inserted between adjacent ribs "R" (FIG. 19) of a patient, i.e., through thoracic access portal 300 (FIGS. 18-19) disposed within an incision "I" (FIGS. 18-19) in the intercostal space.

As mentioned above, shaft 200 includes a plunger assembly 260 disposed at proximal end 204 thereof, an end effector assembly 220 disposed at distal end 202 thereof, and an articulation assembly 240 coupled thereto for articulating end effector assembly 220 relative to shaft 200. Further, shaft 200 is slidably positionable within lumen 122 of handle 100 and elongated sleeve 120 and is configured for longitudinal translation therethrough between the retracted position (FIG. 2), wherein shaft 200 is retracted proximally relative to handle 100 and elongated sleeve 120 such that end effector assembly 220 is disposed within lumen 122, i.e., such that end effector assembly 220 does not extend from distal end 126 of sleeve 120, and the deployed position (FIG. 1), wherein shaft 200 is translated distally through lumen 122 such that end effector assembly 220 extends distally from distal end 126 of elongated sleeve 120 to deploy specimen retrieval bag 30.

With continued reference to FIGS. 1-3, shaft 200 includes a bifurcated proximal end 204 and plunger assembly 260 includes a protrusion 262 extending from base 261 thereof that is configured to be received within the bifurcated proximal end 204 of shaft 200. A pin 264 inserted through each of the bifurcated portions of proximal end 204 of shaft 200 and through protrusion 262 of plunger assembly 260 secures plunger assembly 260 to proximal end 204 of shaft 200.

Plunger assembly 260 further includes a handle 265 extending proximally from base 261. Handle 265 defines a central, annular portion 266 having an aperture 267 extending therethrough and a pair of lateral grasping flanges 268 extending outwardly from annular portion 266 to facilitate the grasping of plunger assembly 260 to retract plunger assembly 260 and, thus, shaft 200 relative to handle 100 and elongated sleeve 120, e.g., from the deployed position (FIG. 1) back to the retracted position (FIG. 2).

Figure 16:
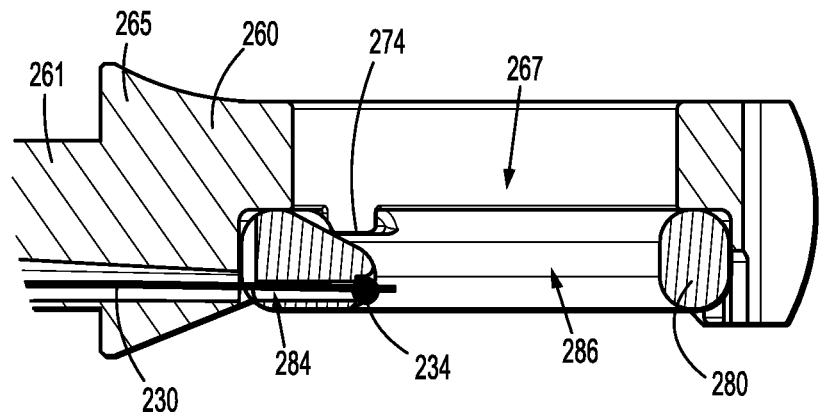
FIG. 16 is an enlarged, longitudinal cross-sectional view of a plunger configured for use with the surgical retrieval apparatus of FIG. 1.
Figure 17:
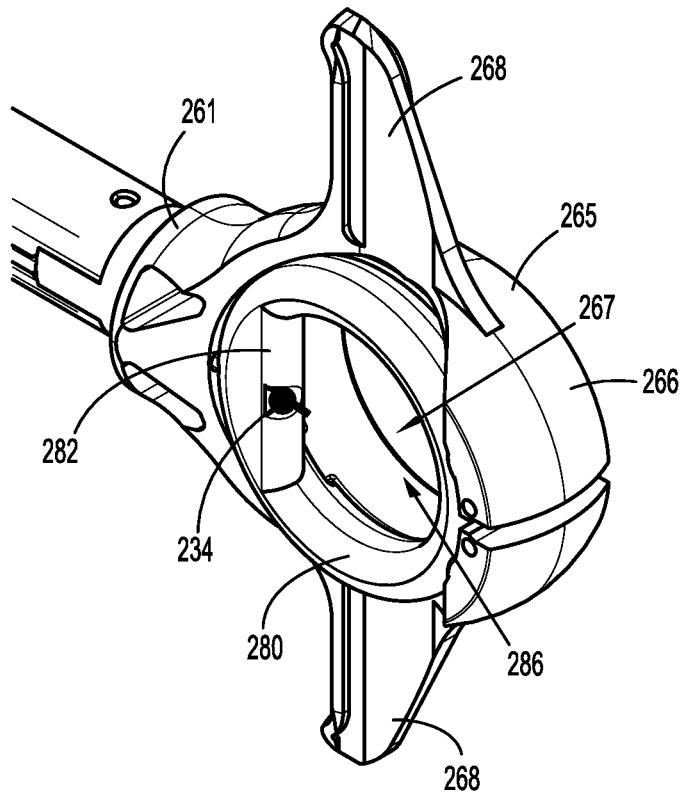
FIG. 17 is a side, perspective view of the plunger of FIG. 16.

A pull-ring 280 is removably disposed within plunger assembly 260. Pull-ring 280 is coupled to cinch cord 230 of specimen retrieval bag 30 and includes a lip 282 extending inwardly into central opening 286 thereof that facilitates the grasping of pull-ring 280 for disengaging pull-ring 280 from plunger assembly 260 and retracting pull-ring 280 relative to plunger assembly 260 to tension cinch cord 230. More specifically, pull-ring 280 is releasably engagable within recessed rim 272 of plunger assembly 260, which is disposed about aperture 267, via a plurality of resilient lock tabs 274 (FIG. 16). A more detailed description of pull-ring 280, including the operation thereof, will be described hereinbelow.

Figure 4:
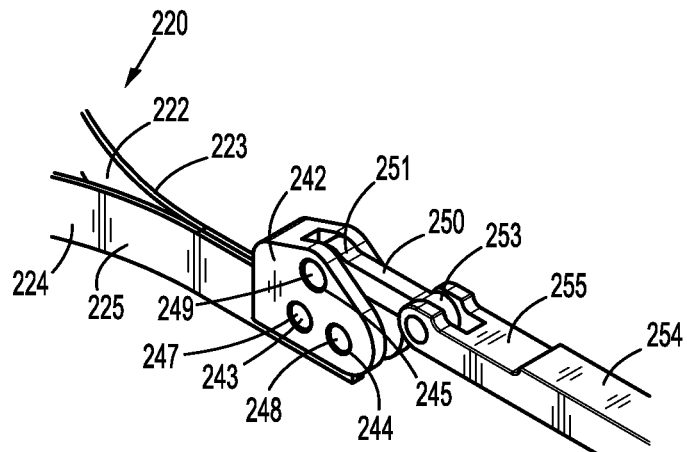
FIG. 4 is an enlarged, perspective view of a distal portion of the surgical retrieval apparatus of FIG. 1, showing an end effector coupled to a shaft thereof.

Continuing with reference to FIGS. 1-3, in conjunction with FIG. 4, end effector assembly 220 is pivotably coupled to shaft 200 and articulation assembly 240. End effect or assembly 220 includes a pair of arms 222, 224 configured for positioning within loop 34 formed at open end 33 of specimen retrieval bag 30 to retain specimen retrieval bag 30 thereon. In the deployed position, as shown in FIG. 1, arms 222, 224 of end effector assembly 220 define a spaced-apart, curvate configuration for retaining specimen retrieval bag 30 thereon in an open condition, although other configurations are also contemplated, e.g., end effector assembly 200 may include non-linear arms 222, 224. Articulation assembly 240 includes a rotatable member 242, an articulation linkage 250, and an articulation bar 254 that is disposed within an elongated, longitudinally-extending recess 206 defined within shaft 200, thus permitting articulation bar 254 to translate through recess 206 relative to shaft 200.

Arms 222, 224 of end effector assembly 220 are pivotably coupled to shaft 200 via rotatable member 242 of articulation assembly 240. More particularly, arms 222, 224 of end effector assembly 220 each include a first aperture 226, 227, respectively, and a second aperture 228, 229, respectively, longitudinally-spaced from first aperture 226, 227, respectively. Apertures 226, 228 and 227, 229 of respective arms 222, 224 are defined therethrough at proximal ends 223, 225, respectively, thereof. Rotatable member 242 similarly includes first and second longitudinally-spaced apertures 243, 244, respectively, defined therethrough. A first pin 247 is secured through first aperture 226 of arm 222, first aperture 243 of rotatable member 242, and first aperture 227 of arm 224. A second pin 248 is secured through apertures 208 defined within each portion of the at least partially bifurcated distal end 202 of shaft 200 and through second apertures 228, 229 of arms 222, 224, respectively, and second aperture 244 of rotatable member 242. As can be appreciated, such a configuration fixedly secures arms 222, 224 and rotatable member 242 to one another, e.g., via the first and second pins 247, 248, respectively, engaged therebetween, and pivotably couples rotatable member 242 and arms 222, 224 of end effector assembly 220 to distal end 202 of shaft 200, e.g., via second pin 248. Alternatively, arms 222, 224 may be overmolded, or otherwise formed with rotatable member 242.

A third pin 249 is disposed through third aperture 245 of rotatable member 242, which is offset above and distally of second pin 248, the pivot point between rotatable member 242 (and end effector assembly 220) and shaft 200. Third pin 249 pivotably couples articulation linkage 250 to rotatable member 242 at first end 251 thereof. Articulation linkage 250 is pivotably coupled to distal end 255 of articulation bar 254 at second end 253 thereof. Articulation bar 254 is disposed within recess 206 of shaft 200 and, as will be described in greater detail below, is longitudinally translatable therethrough to urge, i.e., push or pull, articulation linkage 250.

Pulling articulation linkage 250 proximally, for example, pulls pin 249 proximally, thereby rotating rotatable member 242 and arms 222, 224 about second pin 248 to articulate arms 222, 224 of end effector assembly 220 off of longitudinal axis "X-X," defining an acute angle between arms 222, 224 and longitudinal axis "X-X" of shaft 200. Pushing articulation linkage 250 distally, on the other hand, urges pin 249 distally, thereby rotating rotatable member 242 and arms 222, 224 about second pin 248 to articulate aims 222, 224 of end effector assembly 220 back towards longitudinal axis "X-X" (i.e., back towards the substantially aligned position).

Figure 5:
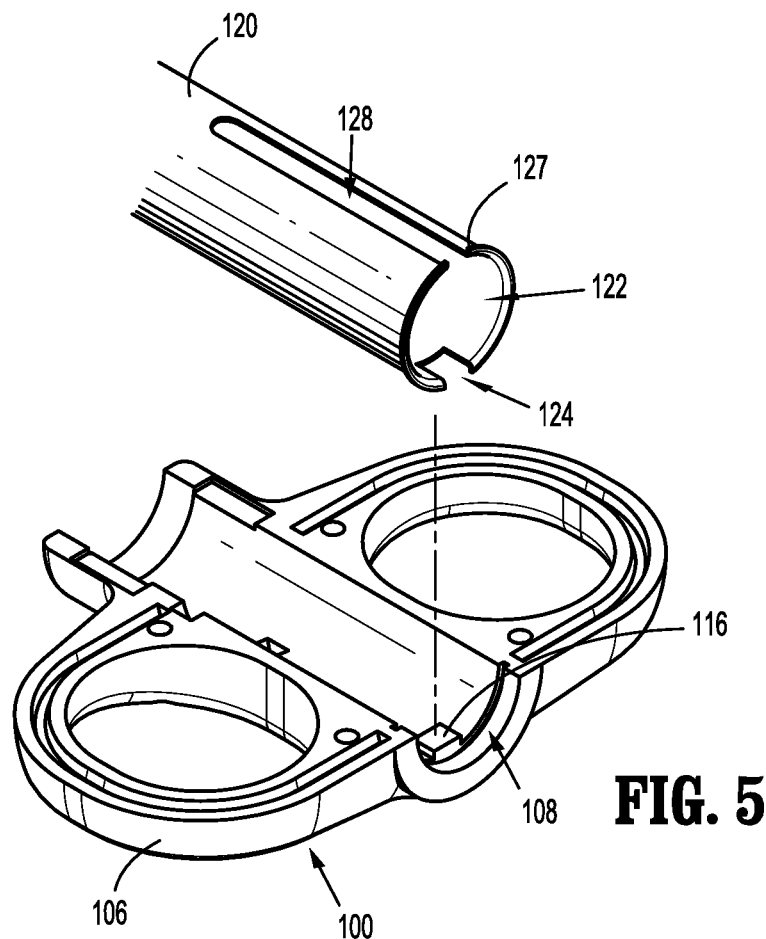
FIG. 5 is an enlarged, perspective view of a proximal portion of the surgical retrieval apparatus of FIG. 1.
Figure 6:
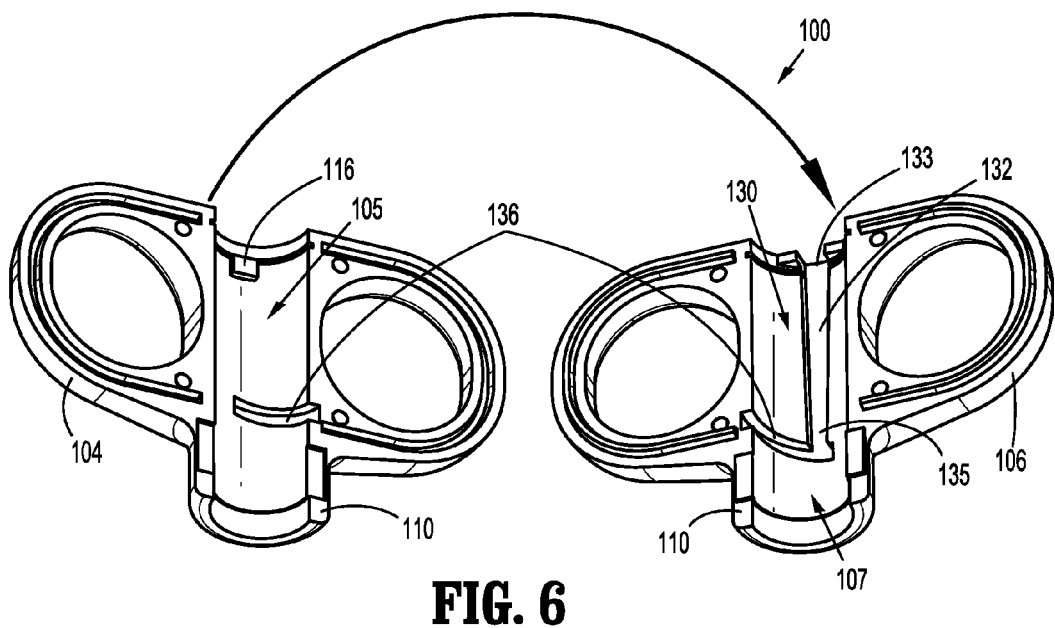
FIG. 6 is an exploded, perspective view of the handle portion of the surgical retrieval apparatus of FIG. 1.
Figure 7:
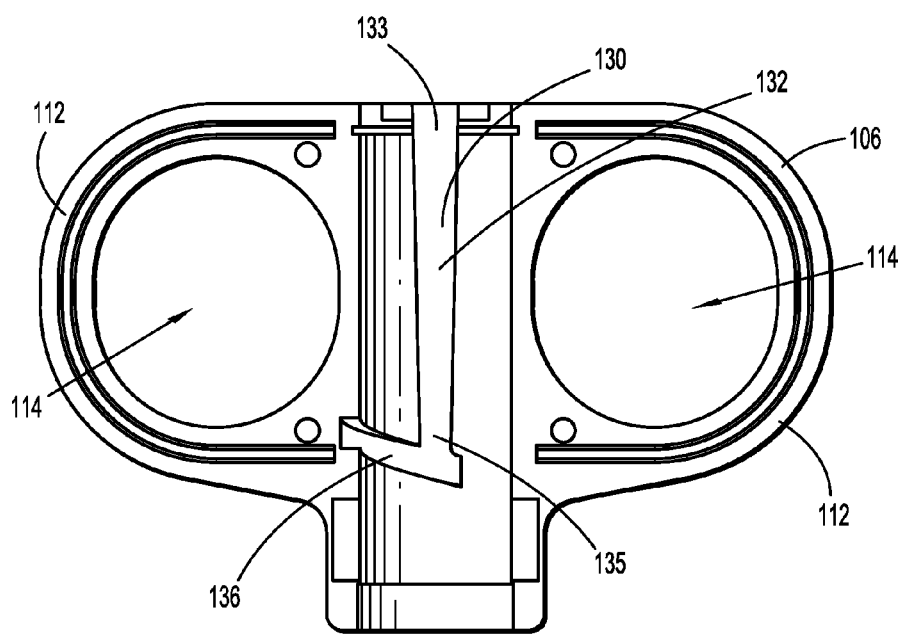
FIG. 7 is a transverse, cross-sectional view of the handle portion of the surgical retrieval apparatus of FIG. 1.
Figure 10:
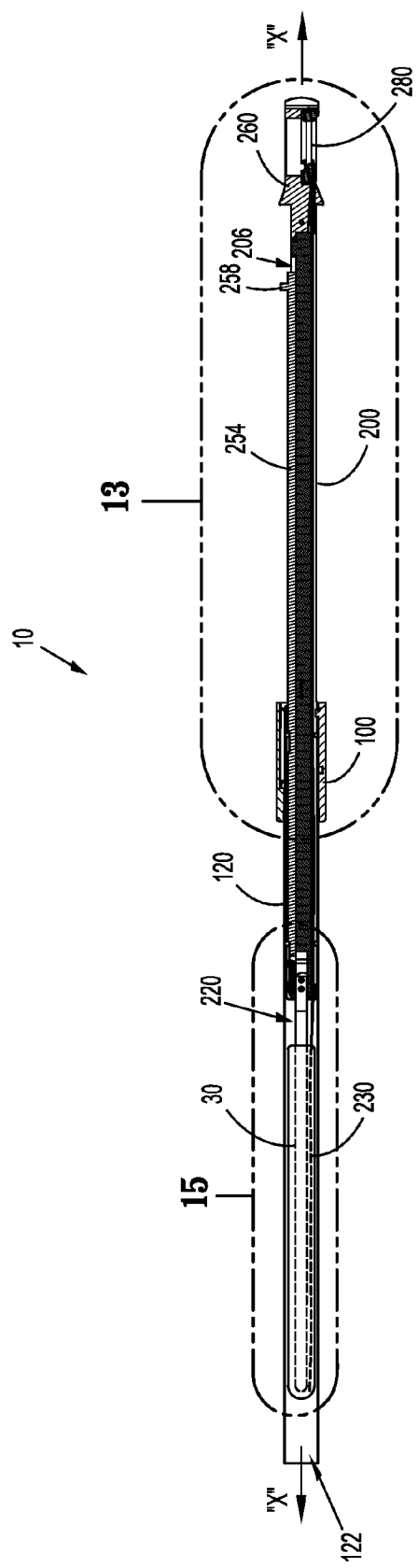
FIG. 10 is a side, longitudinal cross-sectional view of the surgical retrieval apparatus of FIG. 1, shown in the retracted position.

Turning now to FIGS. 5-7, in conjunction with FIGS. 1-3, articulation bar 254 of articulation assembly 240 includes an articulation post 258 extending generally perpendicularly from articulation bar 254 at proximal end 256 thereof. Articulation post 258 defines a height sufficient to extend from recess 206 of shaft 200 such that articulation post 258 engages within articulation track 130 defined on inner surfaces 105, 107 of handle components 104, 106, respectively. As will be described in detail below, with articulation post 258 engaged within articulation track 130, articulation bar 254 may be selectively translated relative to shaft 200 upon selective rotation of handle 100 about longitudinal axis "X-X" relative to shaft 200 to articulate end effector assembly 220 off of longitudinal axis "X-X." More particularly, as best shown in FIG. 5, elongated sleeve 120 includes a longitudinal slot 128 extending from proximal end 127 thereof that is configured to receive articulation post 258 therethrough, thus allowing articulation post 258 to extend from articulation bar 254, shaft 200, through elongated sleeve 120, and into engagement with articulation track 130.

Articulation track 130, as shown in FIGS. 6-7, includes a longitudinal portion 132 and a helical portion 136, and is formed partially within each of handle components 105, 107 such that, upon engagement of handle components 105, 107 to one another, articulation track 130 is fully formed. As mentioned above, articulation track 130 is configured to receive articulation post 258 therein. More specifically, upon translation of shaft 200 from the retracted position (FIG. 2) to the deployed position (FIG. 1) to deploy end effector assembly 220 and specimen retrieval bag 30, articulation post 258 is translated distally along longitudinal portion 132 of articulation track 130 into position adjacent helical portion 136 thereof. Longitudinal portion 132 of articulation track 130 extends generally parallel relative to longitudinal axis "X-X" and inhibits rotation of handle 100 about longitudinal axis "X-X" and relative to shaft 200 when shaft 200 is disposed in the retracted position due to the engagement of articulation post 258 within articulation track 130. Accordingly, articulation of end effector assembly 220 when shaft 200 is disposed in the retracted position is inhibited at both the proximal end 204 of shaft 200, due to the engagement of articulation post 258 within longitudinal portion 132 of articulation track 130, as well as at the distal end 202 of shaft 200, due to the internal dimensions of lumen 122 of elongated sleeve 120, which inhibit substantial movement of end effector assembly 200 off of longitudinal axis "X-X" when disposed therein.

Figure 18:
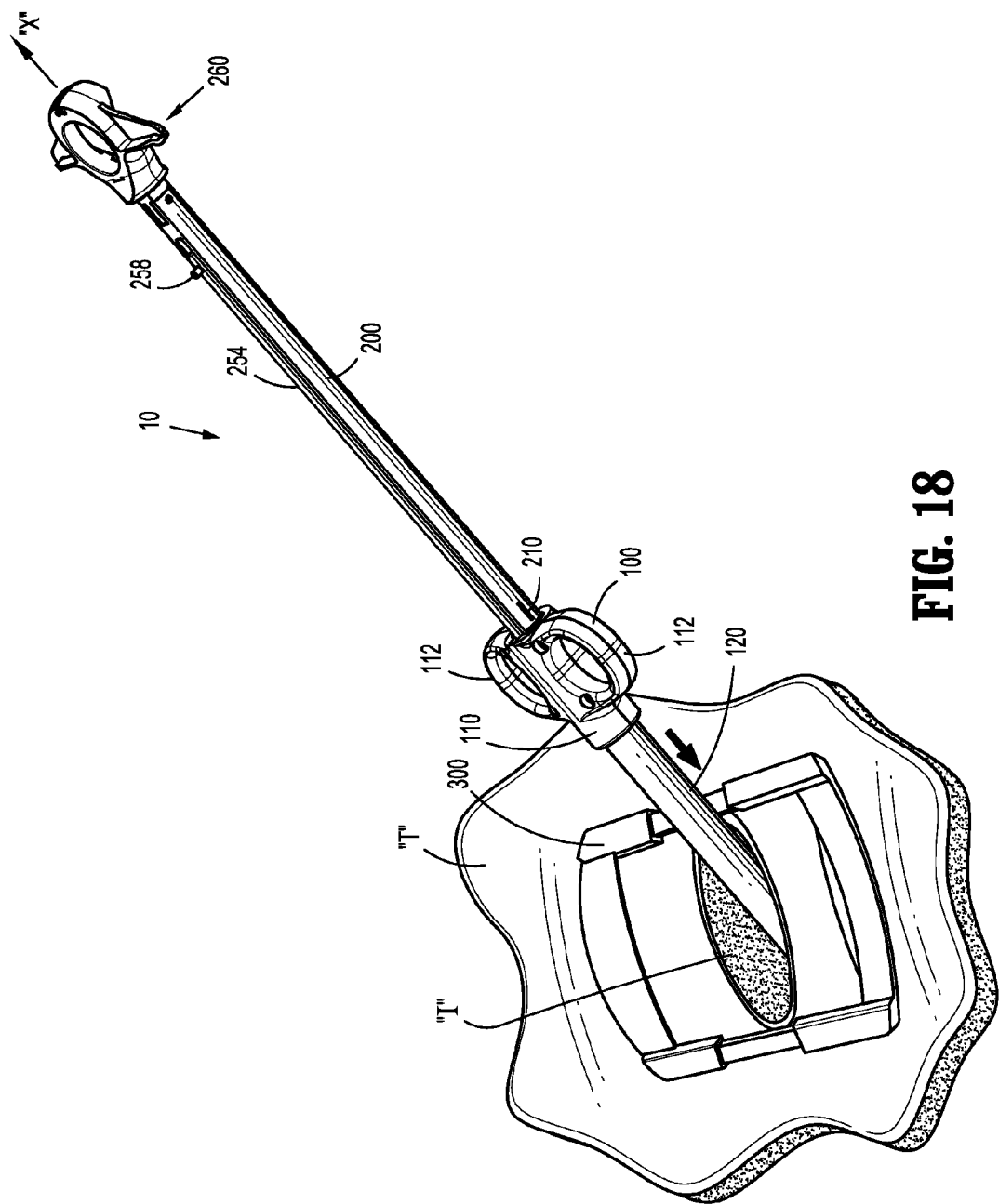
FIG. 18 is a side, perspective view of the surgical retrieval apparatus of FIG. 1, shown being inserted through an incision in tissue.
Figure 19:
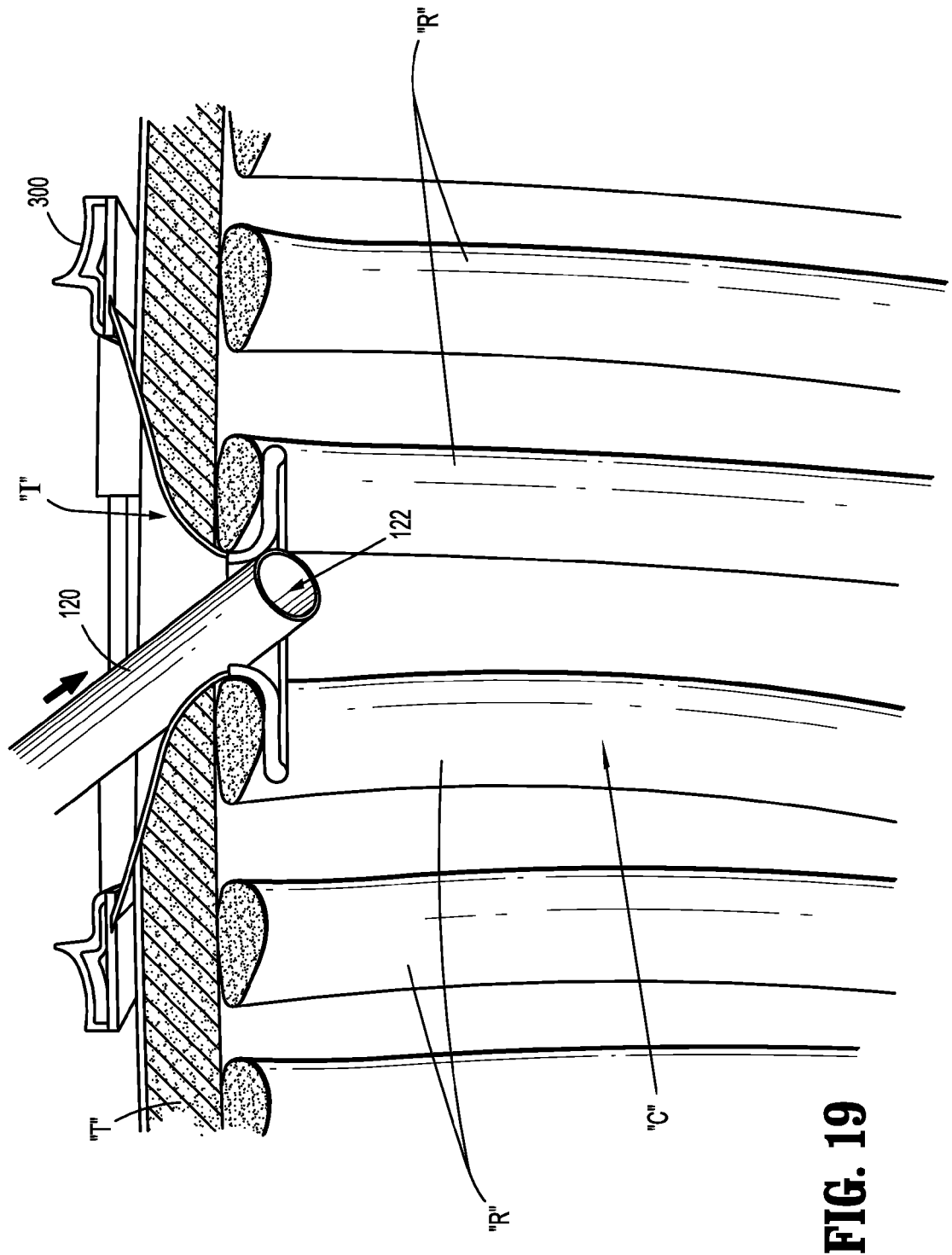
FIG. 19 is a transverse, cross-sectional view of the surgical retrieval apparatus of FIG. 18, shown being inserted through an incision in tissue and into an internal surgical site (e.g., the thoracic cavity)

With reference to FIGS. 1-3 and 5-7, upon translation of shaft 220 to the deployed position, however, articulation post 258 is translated along longitudinal portion 132 of articulation track 130 into position adjacent helical portion 136 of articulation track 130. In this position, handle 100 may be rotated about longitudinal axis "X-X" and relative to shaft 200 to translate articulation post 258 through helical portion 136 and relative to shaft 200. Further, with end effector assembly 220 extending from lumen 122 of elongated sleeve 120, arms 222, 224 are no longer confined within lumen 122 elongated sleeve 120. Thus, as can be appreciated, translation of articulation post 258 through helical portion 136 of articulation track 130 may be effected to translate articulation post 258 and, thus, articulation bar 154 relative to shaft 200 to articulate of end effector assembly 220 relative to longitudinal axis "X-X." Such articulation provides increased flexibility in the placement of specimen retrieval bag 30 within the body cavity, e.g. thoracic cavity "C" (FIG. 19). It also enables specimen retrieval bag 30 to be placed away from the immediate space adjacent the main access incision "I" (FIGS. 18-19) and placed towards the apex of the cavity "C" (FIG. 19). This provides the surgeon with a functional space immediately below the incision "I" (FIGS. 18-19) where the specimen "S" (FIG. 19) can be easily and directly manipulated and where the space can be visualized from the separate scope port (not shown). That is, the bag 30 can be out of the way of loading and visualization.

Referring now to FIGS. 8-9, in conjunction with FIG. 3, specimen retrieval bag 30 is removably coupled to end effector assembly 220 and depends therefrom. More specifically, specimen retrieval bag 30 is folded over at an open end 33 thereof to form a loop 34 around the outer periphery thereof. End effector assembly 220 includes a pair of arms 222, 224 configured for removable positioning within loop 34 formed at open end 33 of specimen retrieval bag 30 to retain specimen retrieval bag 30 thereon. In the deployed position, as shown in FIG. 1, arms 222, 224 of end effector assembly 220 define a spaced-apart, curvate configuration for retaining specimen retrieval bag 30 thereon in an open condition, although other configurations are also contemplated, e.g., end effector assembly 220 may include linear arms 222, 224. In the retracted position, on the other hand, arms 222, 224 of end effector assembly 220 are disposed in a substantially-straight configuration in close proximity to one another to permit positioning within and translation through lumen 122 of elongated sleeve 120. As will be described below, arms 222, 224 may be biased toward the spaced-apart, curvate configuration such that, upon reaching the deployed position, arms 222, 224 are automatically deployed, i.e., arms 222, 224 are resiliently returned, to the spaced-apart curvate configuration, thus transitioning specimen retrieval bag 30 to the open condition.

Continuing with reference to FIGS. 8-9, in conjunction with FIG. 3, as will be described in greater detail below, a cinch cord 230 is disposed through loop 34 of specimen retrieval bag 30. First and second ends 232, 234, respectively, of cinch cord 230 extend proximally from loop 34 of specimen retrieval bag 30. One of the ends, e.g., first end 232, is looped about the other end, e.g., second end 234, and is knotted, or otherwise secured about itself (see FIG. 23), while second end 234 extends proximally though shaft 200, ultimately engaging, i.e., knotting about, pull-ring 280. Accordingly, as will be described in greater detail below, upon translation of pull-ring 280 proximally relative to shaft 200, cinch cord 230 is likewise pulled proximally to tension cinch cord 230 such that specimen retrieval bag 30 is cinched closed. Upon retraction of the apparatus, arms 222, 224 slide out of the loop 34 and the cord 230 is cut, prefereably by a knife in the handle portion to separate the bag and cord from the instrument.

With continued reference to FIGS. 8-9, in conjunction with FIG. 3, it is envisioned that specimen retrieval bag 30 be formed from any suitable bio-compatible material (or materials), e.g., 30 Denier Ripstop Nylon, configured to retain a specimen of tissue "S" (FIG. 29) therein and to inhibit the passage of fluids and biological materials therethrough. The bag 30 can include a coating, such as a polyurethane coating, to prevent egress of fluid if a permeable bag is utilized or to improve the impermeability. The coating can be placed on the inner surface and/or the outer surface of the bag 30. Specimen retrieval bag 30 includes a lower portion 32 having a minimized cross-section configured to re-orient or re-position the specimen of tissue "S" (FIG. 29) within specimen retrieval bag 30 to facilitate removal of specimen retrieval bag 30 from an internal body cavity, and a relatively expansive upper portion 35 configured to facilitate positioning of relatively large specimen of tissue "S" (FIG. 29) within specimen retrieval bag 30. In other words, lower portion 32 has a smaller transverse dimension than upper portion 35. More specifically, upper portion 35 of specimen retrieval bag 30 has a first side 36 and a generally-angled side 37 disposed opposite first side 36. Angled side 37 tapers inwardly such that the transverse dimension of upper portion 35 of specimen retrieval bag 30 progressively decreases toward the lower portion 32 of specimen retrieval bag 30. Wall 38, which opposes wall 39 in lower portion 32 of specimen retrieval bag 30, extends substantially parallel to wall 39 such that the transverse dimension of lower portion 32 remains substantially constant along a length thereof. Alternatively, specimen retrieval bag 30 may be formed in various other configurations depending on the intended use of specimen retrieval bag 30.

As mentioned above, open end 33 of upper portion 35 of specimen retrieval bag 30 includes a loop 33 defined about the outer periphery thereof. Loop 33 is configured to receive arms of end effector assembly 220 and cinch cord 230 therethrough for retaining specimen retrieval bag 30 on end effector assembly 220 and for cinching, or closing specimen retrieval bag 30, respectively.

Specimen retrieval bag 30 may in some embodiments further include a high-friction mesh material disposed on an inner surface thereof to facilitate retention of the tissue specimen "S" (FIG. 29) therein. In other embodiments, the bag shape is relied on to retain the specimen "S" (FIG. 29) and a smooth inner surface is provided to enable easy passage of the tissue specimen "S" (FIG. 29) from the upper loading area, i.e., upper portion 35, of the bag 30 to the lower shaping region, i.e., lower portion 32, of the bag 30 during extraction.

Specimen retrieval bag 30 further includes a channel 42 formed therein. The channel 42 can be formed as integral with the bag material or alternatively can be in the form of a separate tube attached to the bag 30, e.g. attached to an inner surface. The channel 42 includes at least one opening or slot 44 along its length to allow the passage of air into the channel 42. Preferably, a plurality of slots or openings are provided to enable communication between the air and/or fluid in the bag 30 and the interior of the channel 42. The channel 42 in some embodiments can also terminate at its distal end spaced from the bottom of the bag 30 to communicate at a distal opening with the interior of the bag 30 to provide another path for the escape of air fluid. Further, the proximal end of channel 42, in some embodiments, may be open to communicate with the exterior of the bag 30.

A support member (or support members) 40 may be disposed within specimen retrieval bag 30 to help inhibit collapse of the channel 42 and/or for biasing specimen retrieval bag 30 toward an open position upon deployment from surgical retrieval apparatus 10. Support member 40 may be formed from, for example, an open cell material such as open cell foam, or other suitable material that enables the passage of air and/or fluid therethrough, thus allowing air and/or fluid to escape specimen retrieval bag 30 upon collapse or compression of specimen retrieval bag 30 to reduce the internal pressure within specimen retrieval bag 30. More specifically, the open cell foam is preferably of a transverse cross-section less than the transverse cross-section of the channel 42. In this manner, air and/or fluid entering the channel 42 from the bag 30 can flow around the foam material through the channel 42. Note that due to the open cell foam, the air or fluid can also flow through the open cell foam itself. This way, if the channel 42 collapses or is compressed during specimen retrieval, air and fluid can still escape. The escape of air and fluid is caused as the pressure is applied to the bag 30 during withdrawal through access port 300 (FIG. 18), or body opening. As the bag 30 is compressed, the air and/or fluid is forced proximally through the channel 42, exiting the open proximal end thereof. Thus, this decrease in pressure prevents balling of the specimen "S" (FIG. 33) at the bottom of the bag 30 and facilitates removal.

Turning now to FIGS. 10-34, the use and operation of surgical retrieval apparatus 10 will be described along with a more detailed description of the working components of surgical retrieval apparatus 10. Initially, with reference to FIGS. 10-17, surgical retrieval apparatus 10 is disposed in the retracted position, wherein shaft 200 extends proximally from handle 100 and wherein end effector assembly 220 and specimen retrieval bag 30 are disposed within lumen 122 of elongated sleeve 120.

Figure 11:
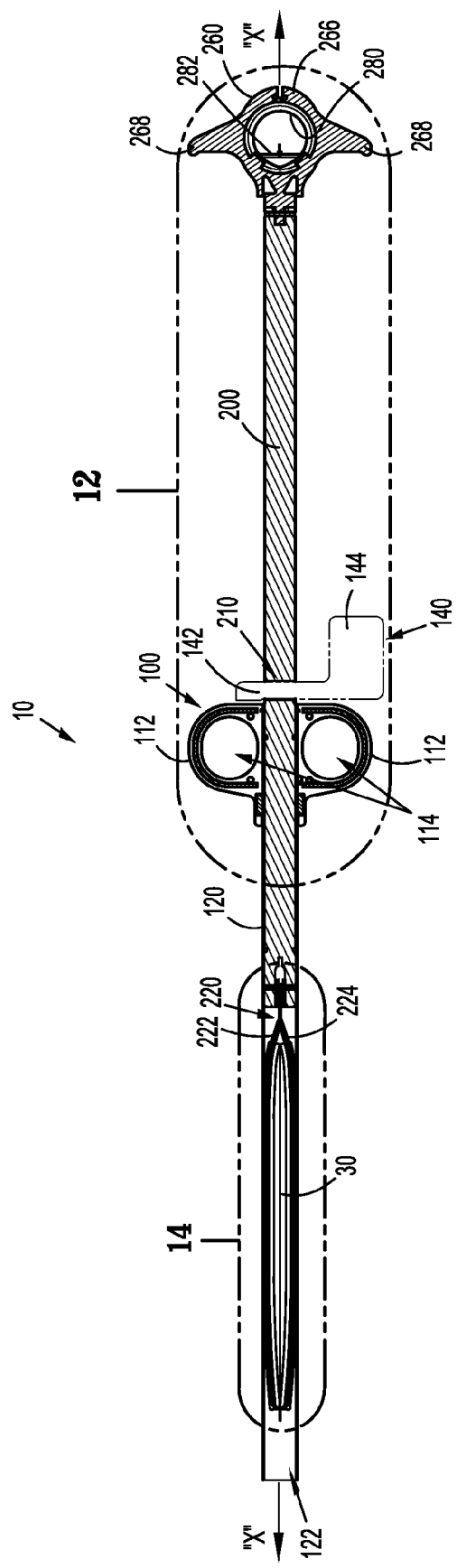
FIG. 11 is a top, longitudinal cross-sectional view of the surgical retrieval apparatus of FIG. 1, shown in the retracted position.

As best shown in FIGS. 11-12, shaft 200 may be configured to receive a safety tab 140 therethrough to inhibit accidental or premature deployment of shaft 200 and specimen retrieval bag 30. More specifically, safety tab 140 is configured to extend through slot 210 defined within shaft 200 and to abut the proximal end of handle 100 to inhibit shaft 200 from being translated further distally through handle 100, thereby inhibiting deployment of end effector assembly 220 and specimen retrieval bag 30. More specifically, safety tab 140 includes a elongated portion 142 for insertion though slot 210 of shaft 200, and an external grasping portion 144 to facilitate grasping by the clinician for removal of safety tab 140 from shaft 200, thus permitting distal advancement (and proximal retraction) of shaft 200 through handle 100 and elongated sleeve 120 towards the deployed position (and retracted position).

Continuing with reference to FIGS. 10-17, in the retracted position, the internal dimensions of lumen 122 of elongated sleeve 120 retain arms 222, 224 of end effector assembly 220 therein in the substantially-straight, approximated position with specimen retrieval bag 30 rolled-up, or wrapped about arms 222, 224. In this position, first and second ends 232, 234 of cinch cord 230 extend from either end of loop 34 of specimen retrieval bag 30 proximally therefrom. More specifically, as mentioned above, first end 232 of cinch cord 230 is looped about second end 234 thereof and is knotted to itself (see FIG. 23), while second end 234 of cinch cord 230 extends through shaft 200, ultimately engaging pull-ring 280, e.g., passing through an aperture 284 defined within pull-ring 280 and knotting on a proximal side thereof. Pull-ring 280 is initially engaged within plunger assembly 260 and, thus, cinch cord 230 is relatively un-tensioned. More particularly, pull-ring 280 is retained within recessed proximal portion 272 of plunger assembly 260 via resilient lock tabs 274.

In preparation for use, and with surgical retrieval apparatus 10 disposed in the retracted position, safety tab 140 is removed, thus permitting advancement of shaft 200 from the retracted position to the deployed position. Next, as shown in FIGS. 18-19, surgical retrieval apparatus 10, lead by elongated sleeve 120, is inserted through thoracic access portal 300 positioned within an incision "I" in tissue "T" between adjacent ribs "R" of a patient, although surgical retrieval apparatus 10 may be directly inserted through the incision "I," or may be used in conjunction with any other suitable thoracic access portal (not shown). As can be appreciated, in this retracted position, since end effector assembly 220 does not extend from elongated sleeve 120, surgical retrieval apparatus 10 defines a reduced diameter to facilitate passage of elongated sleeve 120 through access portal 300, between adjacent ribs "R" of the patient, and into the internal surgical site, e.g., the thoracic cavity "C."

With reference now to FIGS. 18-23, once surgical retrieval apparatus 10 has been inserted into the internal surgical site "C," e.g., the thoracic cavity, shaft 200 may be translated distally through lumen 122, e.g., via grasping handle 100 and plunger assembly 260 and translating plunger assembly 260 distally relative to handle 100, from the retracted position to the deployed position such that end effector assembly 220 is extended from elongated sleeve 120, to deploy arms 222, 224, and specimen retrieval bag 30. More specifically, shaft 200 is translated distally through lumen 122 until end effector assembly 220 extends distally from elongated sleeve 120.

Figure 22:
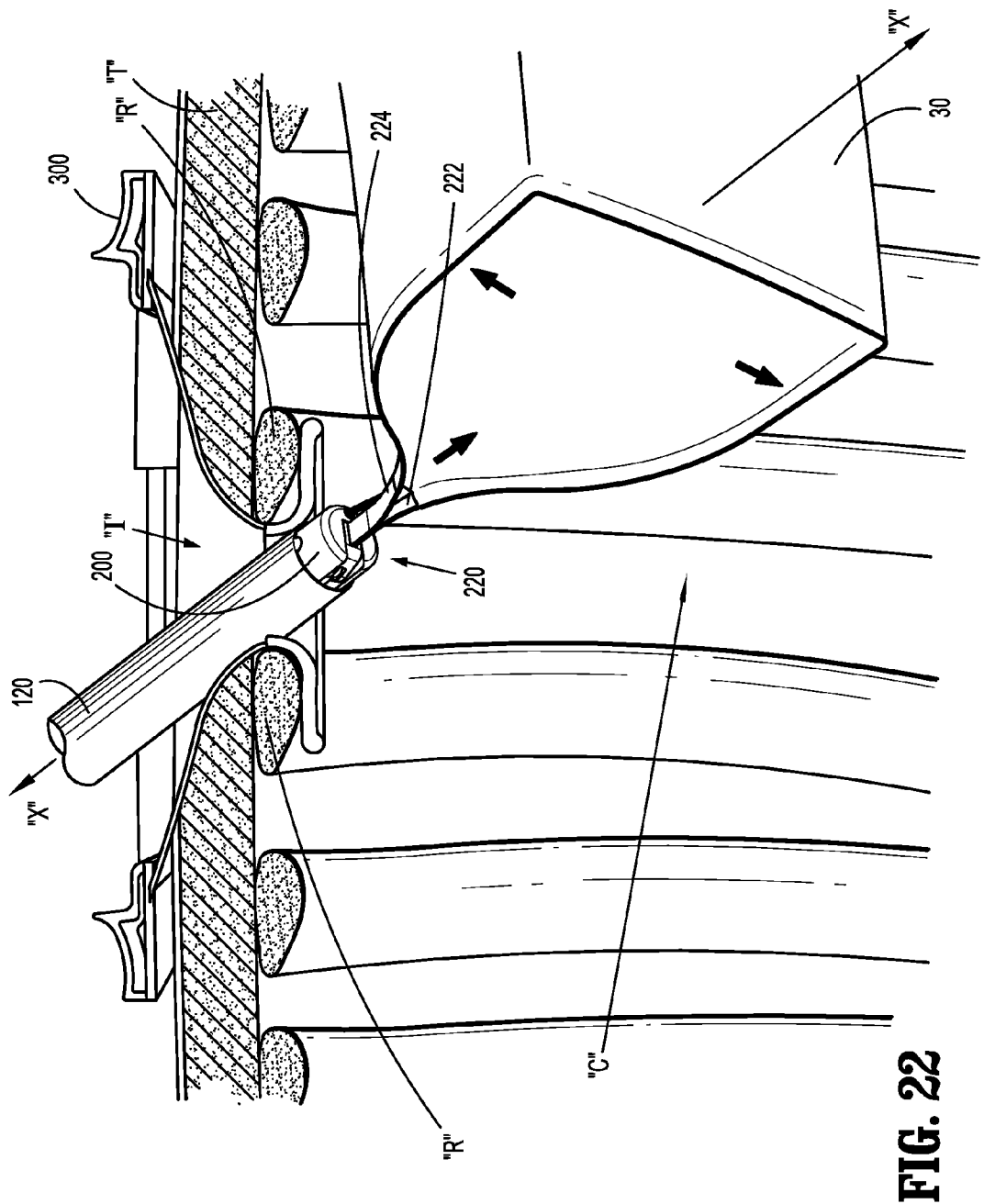
FIG. 22 is a transverse, cross-sectional view of the surgical retrieval apparatus of FIG. 1, shown disposed within an internal surgical site in the deployed position.
Figure 23:
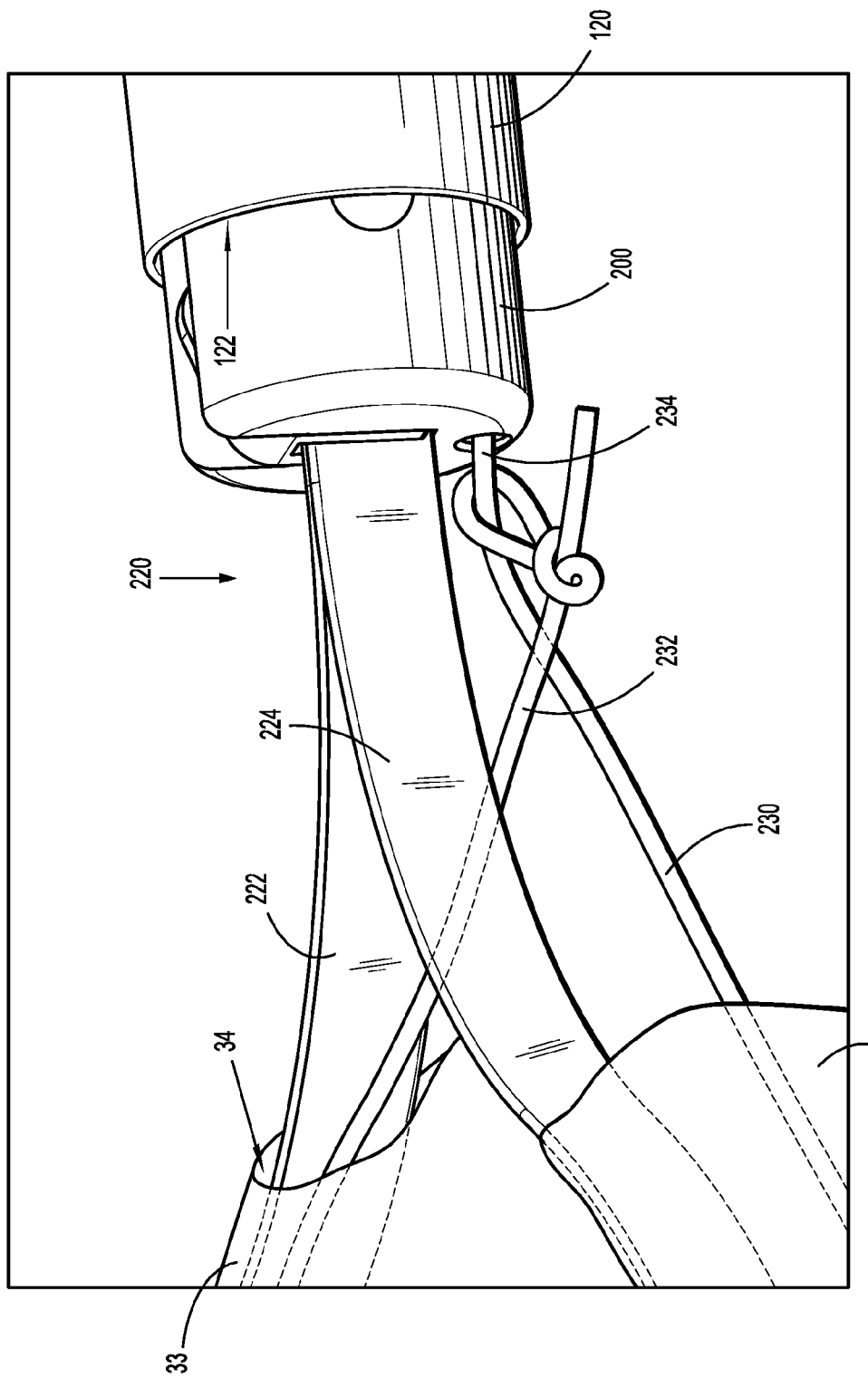
FIG. 23 is an enlarged, side perspective view of a proximal end of an end effector assembly of the surgical retrieval apparatus of FIG. 1, showing a cinch cord of the specimen retrieval bag thereof.
Figure 24:
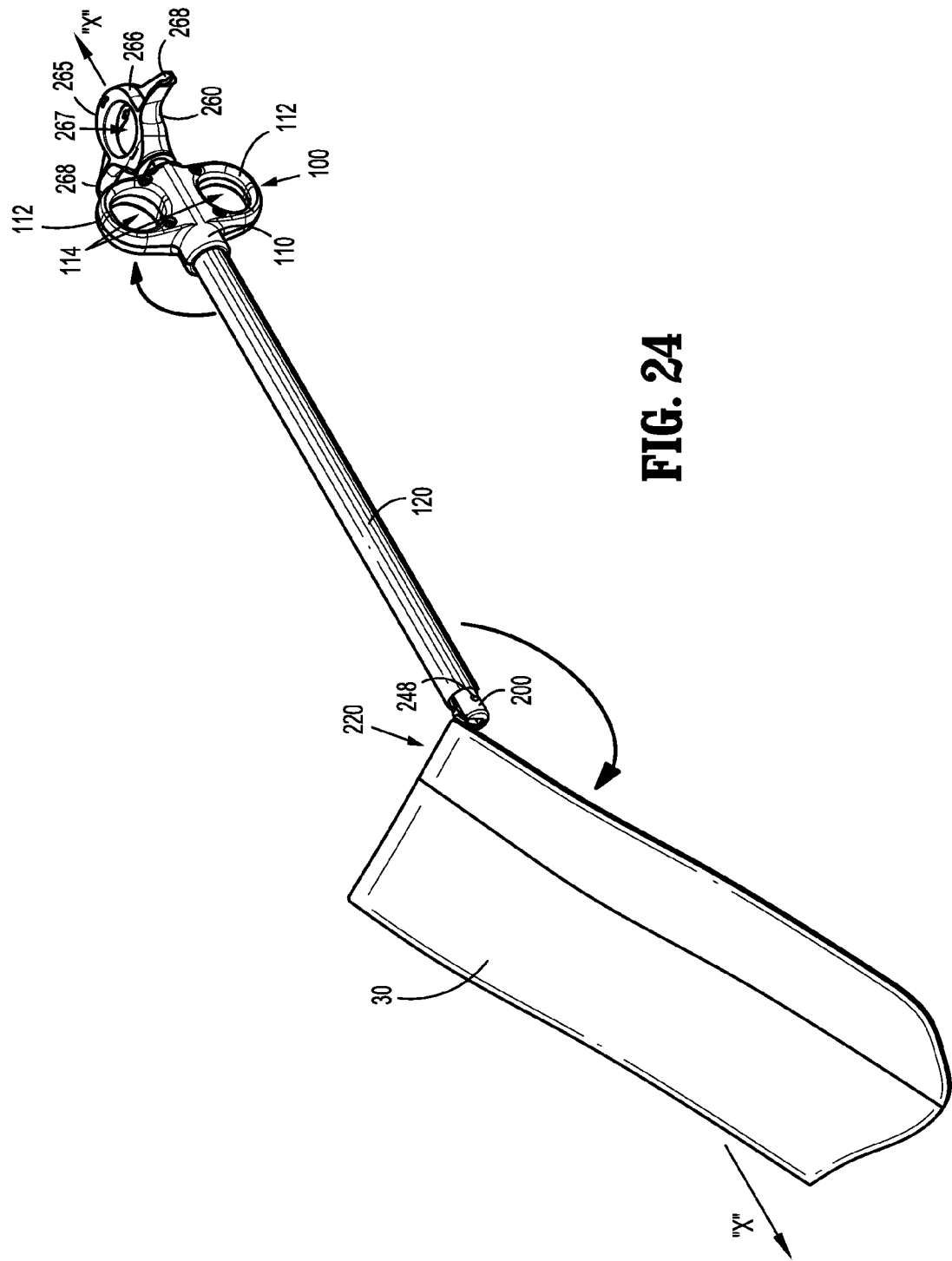
FIG. 24 is a side, perspective view of the surgical retrieval apparatus of FIG. 1, shown in an articulated position.
Figure 27:
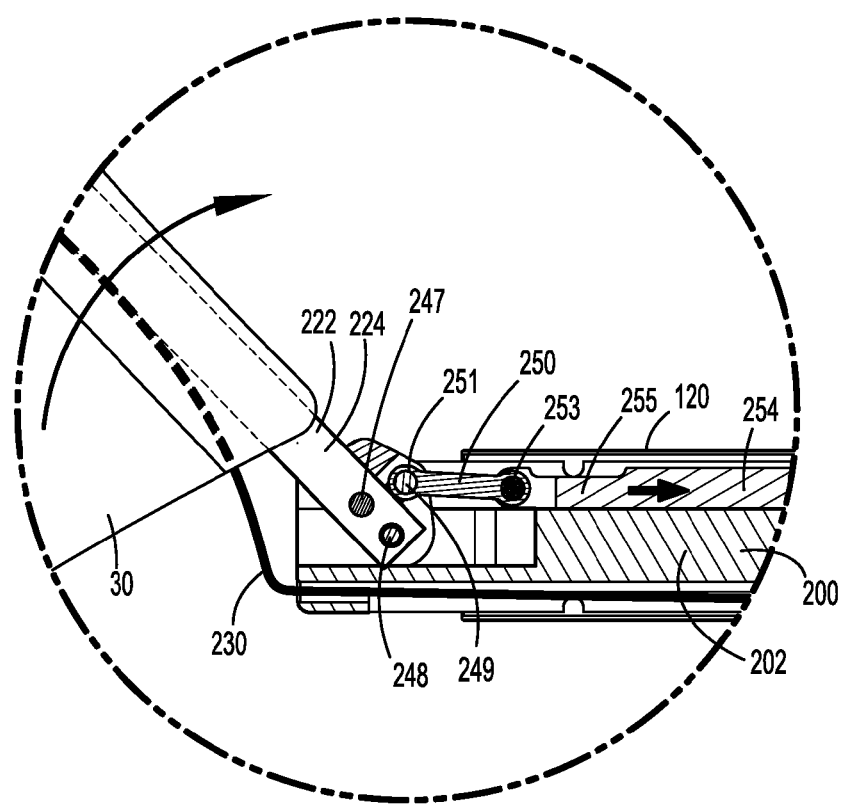
FIG. 27 is an enlarged, longitudinal cross-sectional view of the distal end of the surgical retrieval apparatus of FIG. 1, shown in the articulated position.
Figure 28:
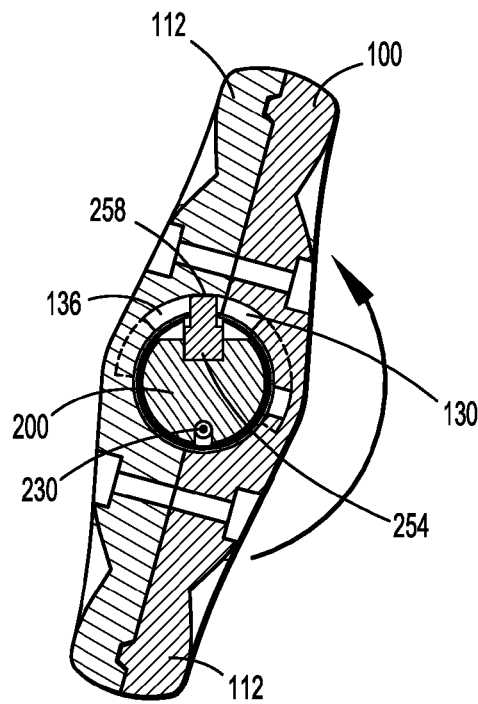
FIG. 28 is a transverse, cross-sectional view of the proximal end of the surgical retrieval apparatus of FIG. 1 taken along line 27-27 of FIG. 25 and in the articulated position.

As can be appreciated, as end effector assembly 220 emerges from elongated sleeve 120, specimen retrieval bag 30 is deployed, or unrolled, to the open condition, as shown in FIGS. 22-23. More specifically, the bias of support member 40 disposed within specimen retrieval bag 30 and the biasing of arms 222, 224 of end effector assembly 220 towards the spaced-apart, curvate configuration automatically transition specimen retrieval bag 30 to the open condition, wherein specimen retrieval bag 30 depends from aims 222, 224 of end effector assembly 220, upon deployment from elongated sleeve 120. Further, first and second ends 232, 234 of cinch cord 230 extend from specimen retrieval bag 30 in a substantially un-tensioned condition due to the maintained engagement of pull-ring 280 within plunger assembly 260 (see FIGS. 16-17), thus maintaining specimen retrieval bag 30 in the open condition.

Continuing with reference to FIGS. 18-23 and to FIGS. 20-21 in particular, at this point, with end effector assembly 220 of surgical retrieval apparatus 10 disposed within the internal surgical site "C" in the deployed condition, end effector assembly 220 remains disposed in an unarticulated position, substantially aligned with longitudinal axis "X-X." However, upon translation of shaft 200 to the deployed position, articulation post 258 is translated distally along longitudinal portion 132 of articulation track 130 defined within handle 100 from proximal end 133 thereof to distal end 135 thereof, wherein articulation post 258 is positioned adjacent helical portion 136 of articulation track 130. Thus, once the deployed position has been achieved, end effector assembly 220 may be articulated to a desired position, or orientation, within the internal surgical site "C," as will be described in greater detail below.

Referring now to FIGS. 24-29, in order to better position specimen retrieval bag 30 within the internal body cavity "C," end effector assembly 220 may be articulated off of longitudinal axis "X-X" to facilitate capturing of the specimen of tissue "S" within surgical retrieval bag 30. Surgical retrieval apparatus 10 may then be manipulated and/or additional surgical instrumentation (e.g., a surgical grasper (not shown)) may be used to position the specimen of tissue "S" within specimen retrieval bag 30.

In order to articulate end effector assembly 220 and, thus, specimen retrieval bag 30, the clinician grasps handle 100 with one hand and plunger assembly 260 of shaft 200 with the other hand and rotates handle 100 relative to shaft 200 about longitudinal axis "X-X" in a first direction, e.g., a counter-clockwise direction. Rotation of handle 100 relative to shaft 200 effects likewise rotation of handle 100 relative to articulation bar 254 and articulation post 258. Accordingly, as handle 100 is rotated about longitudinal axis "X-X" in the counterclockwise direction relative to articulation post 258, articulation post 258 is translated into helical portion 136 of articulation track 130. Helical portion 136 of articulation track 130 is pitched such that, as articulation post 258 is translated therethrough upon rotation of handle 100, articulation post 258 is urged proximally, thereby translating articulation bar 254 proximally along recess 206 and relative to shaft 200. Proximal translation of articulation bar 254, in turn, pulls articulation linkage 250 proximally which urges arms 222, 224 of end effector assembly 220 to pivot about second pin 248 relative to shaft 200, thereby articulating end effector assembly 220 off of longitudinal axis "X-X." As can be appreciated, rotation of handle 100 in the opposite direction, e.g., the clockwise direction, translates articulation bar 254 distally, thereby articulating end effector assembly 220 back towards longitudinal axis "X-X." With end effector assembly 220 articulated to the desired position, e.g., the position shown in FIG. 29, the specimen of tissue "S" can then be moved into specimen retrieval bag 30.

Figure 29:
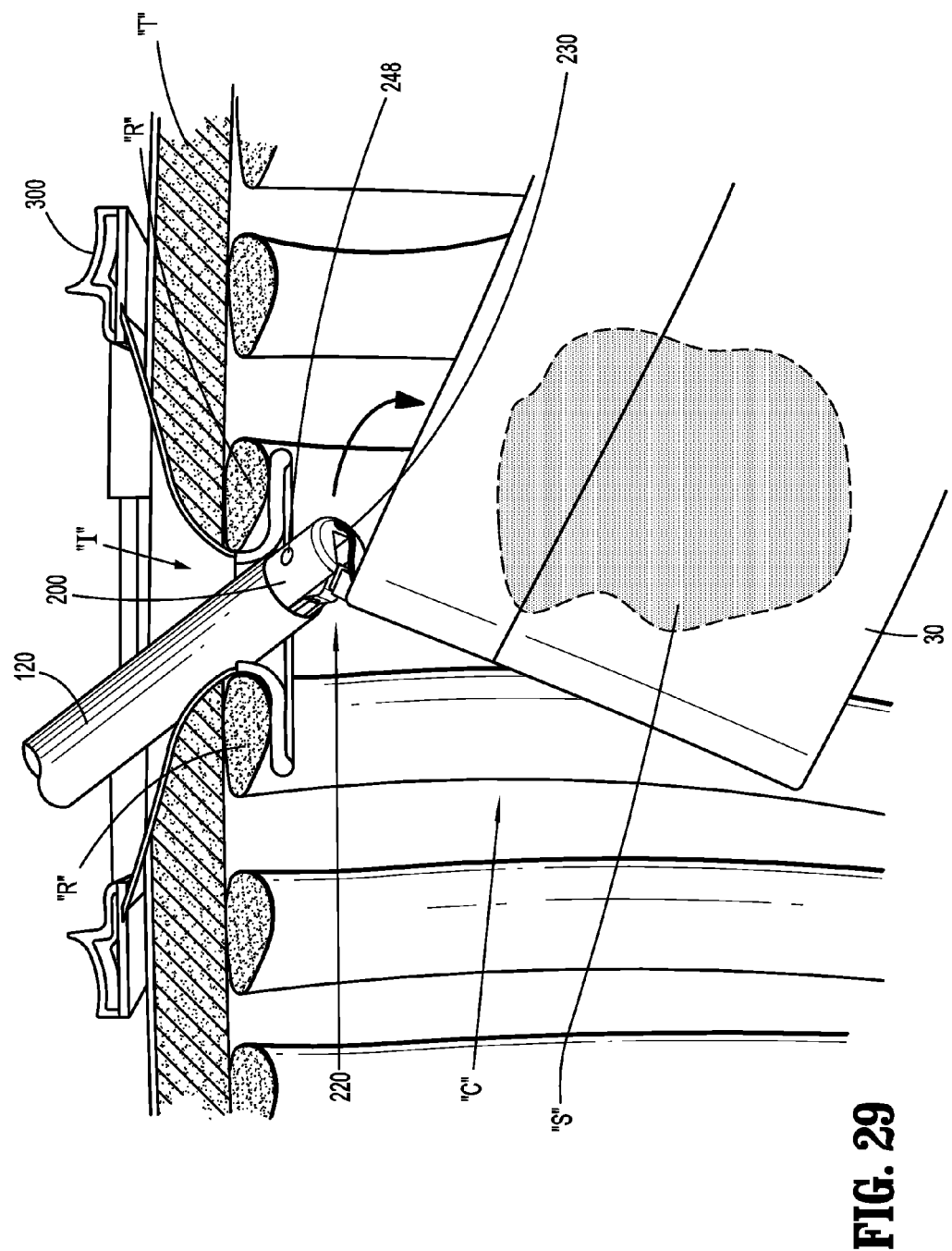
FIG. 29 is a transverse, cross-sectional view of the surgical retrieval apparatus of FIG. 1, shown disposed within an internal surgical site in the deployed and articulated position with a specimen of tissue disposed within the specimen retrieval bag.
Figure 31:
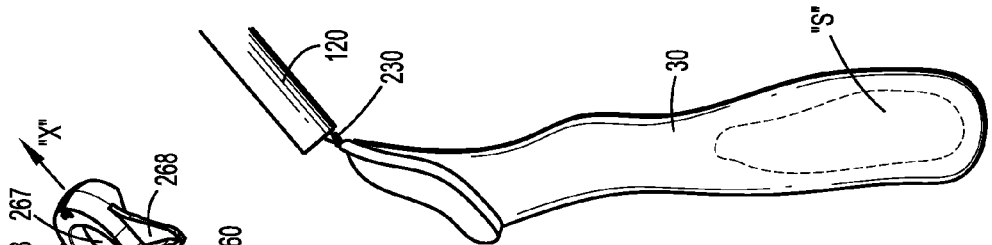
FIG. 31 is a side view of the distal end of the surgical retrieval apparatus of FIG. 1, wherein the specimen retrieval bag is being cinched closed about a specimen of tissue disposed therein.
Figure 30:
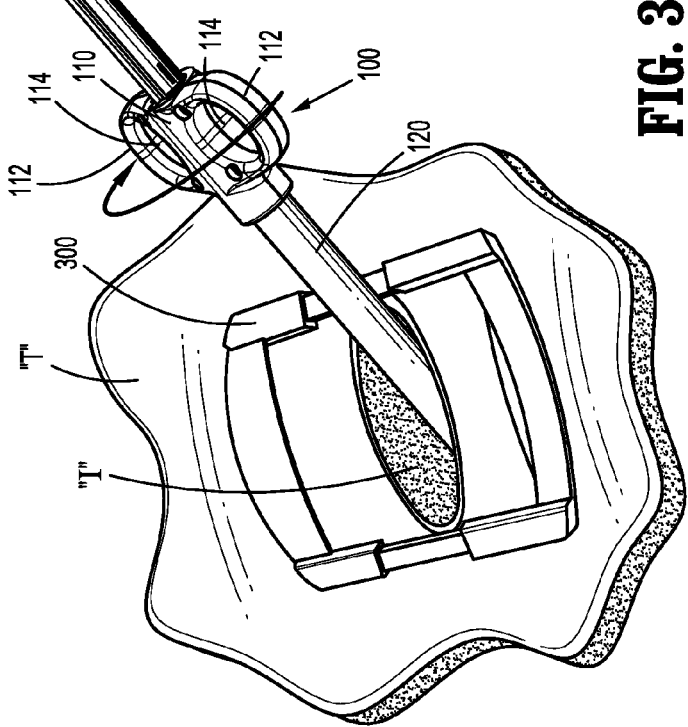
FIG. 30 is a side, perspective view of the surgical retrieval apparatus of FIG. 1, shown inserted through an incision in tissue and returning to the retracted position.

Referring now to FIGS. 29-31, once the specimen of tissue "S" is disposed within specimen retrieval bag 30, specimen retrieval bag 30 may be cinched closed and removed from the internal body cavity "C." In order to cinch closed specimen retrieval bag 30 to secure the specimen of tissue "S" therein, end effector assembly 220 is first returned to the un-articulated position, e.g., via rotating handle 100 relative to shaft 200 in the opposite, e.g. clockwise direction.

Once end effector assembly 220 is aligned with longitudinal axis "X-X," i.e., once end effector assembly 220 is returned to the unarticulated position, plunger assembly 260 is pulled proximally relative to handle 100 from the deployed position back to the retracted position. More specifically, the clinician grasps finger holes 114 of wings 112 of handle 100 with one hand, grasps flanges 268 of plunger assembly 260 with the other hand, and translate plunger assembly 260 and, thus, shaft 200 distally relative to handle 100. Distal translation of shaft 200 relative to handle 100 and elongated sleeve 120 translates arms 222, 224 of end effector assembly 220 proximally into lumen 122 of elongated sleeve 120 and likewise translates cinch cord 230 proximally therethrough to at least partially cinch-closed specimen retrieval bag 30. As shaft 200 is translated distally, arms 222, 224 of end effector assembly 220 are urged toward one another to be accommodated within lumen 122 of sleeve 120 and are withdrawn from loop 34 of specimen retrieval bag 30, thus disengaging specimen retrieval bag 30 from end effector assembly 220, leaving specimen retrieval bag 30 disposed externally and distally of elongated sleeve 120. Further, due to the proximal translation of shaft 200 and, thus cinch cord 230 relative to specimen retrieval bag 30, specimen retrieval bag 30 is at least partially cinched closed as shaft 200 is moved to the retracted position.

Figure 32:
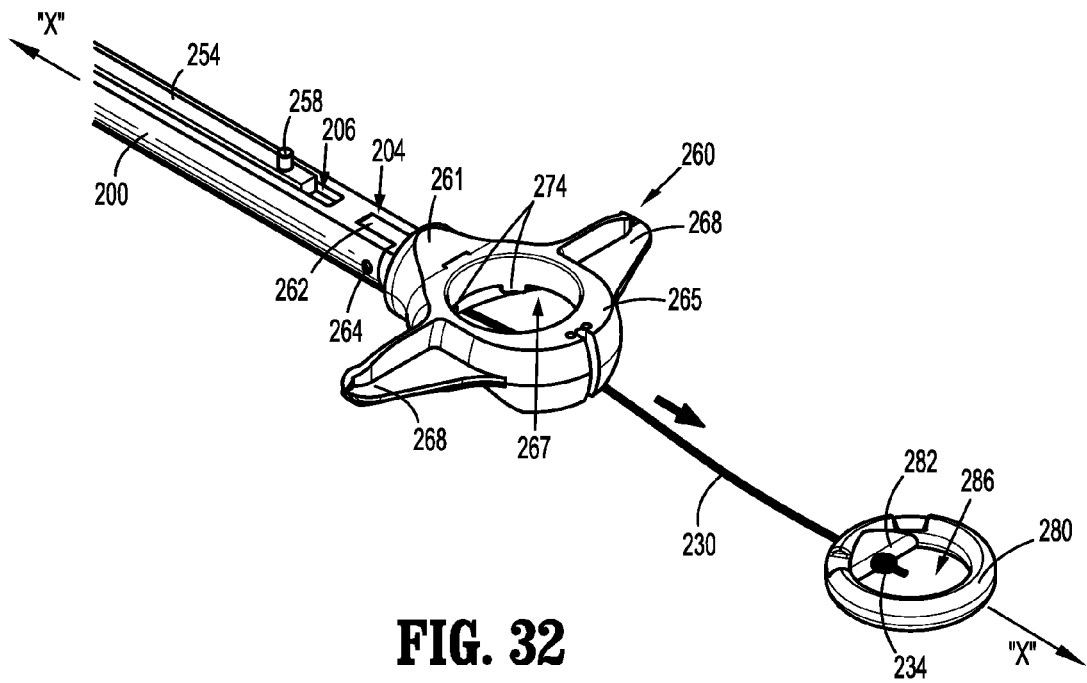
FIG. 32 is a side, perspective view of the proximal end of the surgical retrieval apparatus of FIG. 1, showing a pull-member being translated to cinch closed the specimen retrieval bag.
Figure 33:
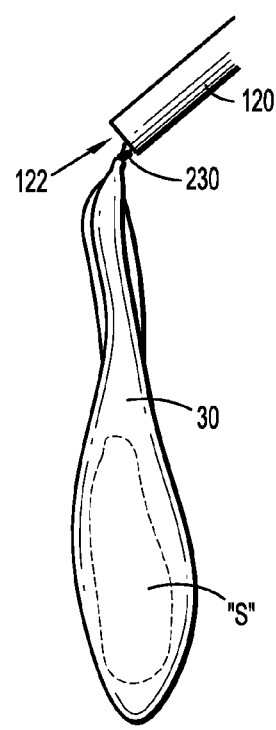
FIG. 33 is a side view of the distal end of the surgical retrieval apparatus of FIG. 1, wherein the specimen retrieval bag has been cinched closed to retain a tissue specimen therein.
Figure 34:
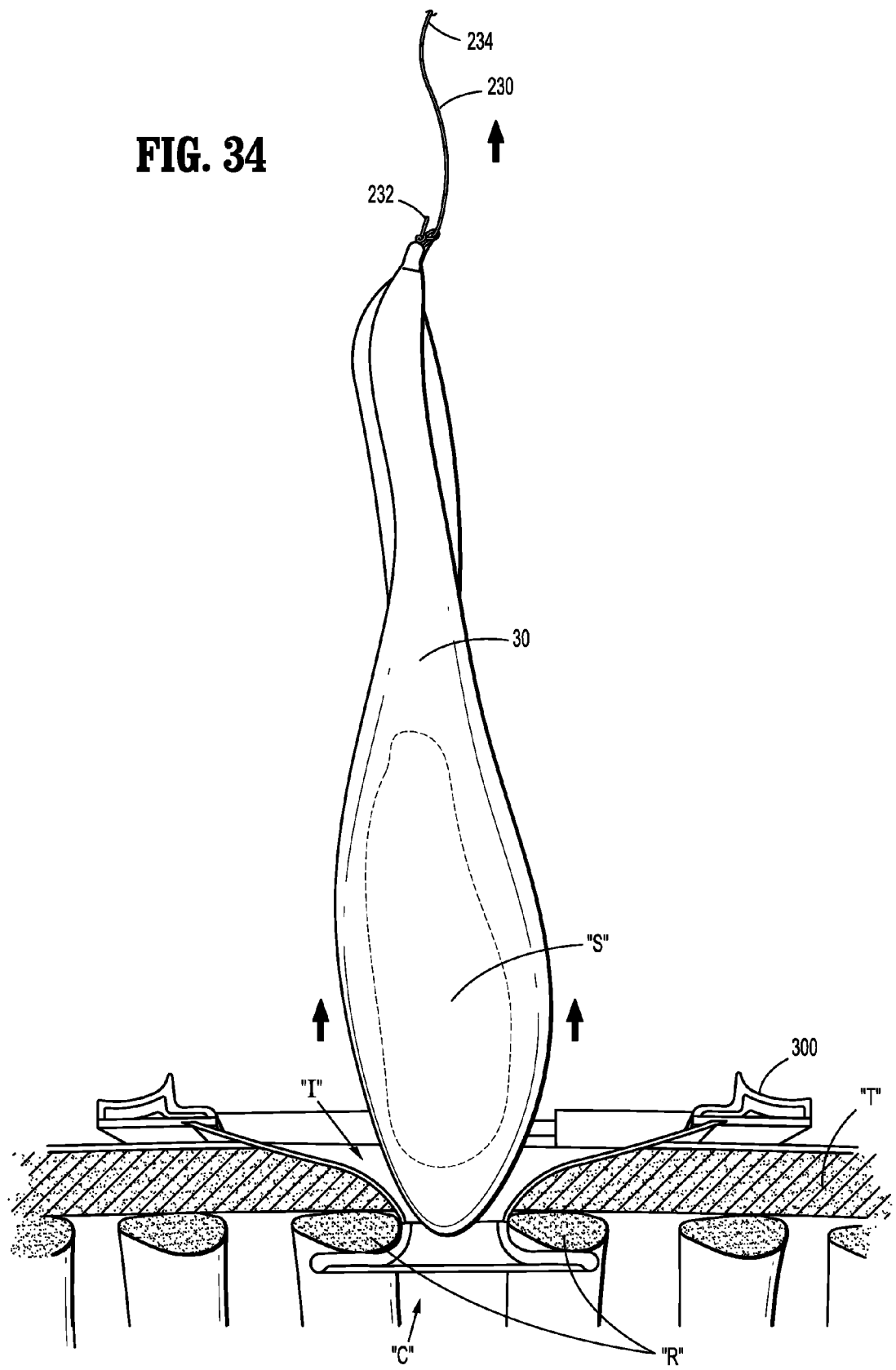
FIG. 34 is a transverse, cross-sectional view showing the specimen retrieval bag being removed through the incision in tissue with a specimen of tissue disposed therein.

Turning now to FIGS. 32-34, in order to fully cinch-closed specimen retrieval bag 30, pull-ring 280 is disengaged from plunger assembly 260 and is translated proximally relative thereto such that second end 234 of cinch cord 230 is translated proximally relative to specimen retrieval bag 30. More specifically, the clinician inserts one or more fingers through opening 286 defined through pull-ring 280 and into recessed rim 272 of plunger assembly 260 to grasp inwardly-extending lip 282 of pull-ring 280. The clinician then translates pull-ring 280 distally with sufficient urging to disengage pull-ring 280 from resilient lock tabs 274 such that pull-ring 280 may be translated proximally with respect to plunger assembly 260 and, thus, shaft 200. As mentioned above, second end 234 of cinch cord 230 is disposed through aperture 284 (FIG. 16) of pull-ring 280 and is knotted on a proximal side thereof such that translating pull-ring 280 relative to plunger assembly 260 translates cinch cord 230 proximally to fully cinch specimen retrieval bag 30 closed, as shown in FIGS. 32-33.

With reference now to FIG. 34, the looping of first end 232 of cinch cord 230 about second end 234 thereof retains cinch cord 230 in position, i.e., the looping of cinch cord 230 inhibits un-tensioning of cinch cord 230, thereby maintaining specimen retrieval bag 30 in the cinched-closed condition. As such, once specimen retrieval bag 30 has been cinched closed with the specimen of tissue "S" disposed therein, cinch cord 230 may be cut to release cinch cord 230 and specimen retrieval bag 30 from the remainder of surgical retrieval apparatus 10, i.e., handle 100, elongated sleeve 120 and shaft 200. These other components of surgical retrieval apparatus 10 may then be removed from the internal surgical site "C" through access portal 300, leaving behind specimen retrieval bag 30, which is disposed in the closed condition with the specimen of tissue "S" therein, and cinch cord 230, which extends from specimen retrieval bag 30 to the second, cut end 234 thereof. More specifically, cinch cord 230 is cut to disengage second end 234 of cinch cord 230 from pull-ring 280, allowing cinch cord 230 to pass through handle 100, elongated sleeve 120, and shaft 200 as these components are withdrawn from the internal surgical site "C," such that specimen retrieval bag 30 and cinch cord 230 remain disposed within the internal surgical site "C." Ultimately, the cut end 234 of cinch cord 230 is translated proximally to remove specimen retrieval bag 30 and the specimen of tissue "S" disposed therein from the internal surgical site "C."

Figure 35:
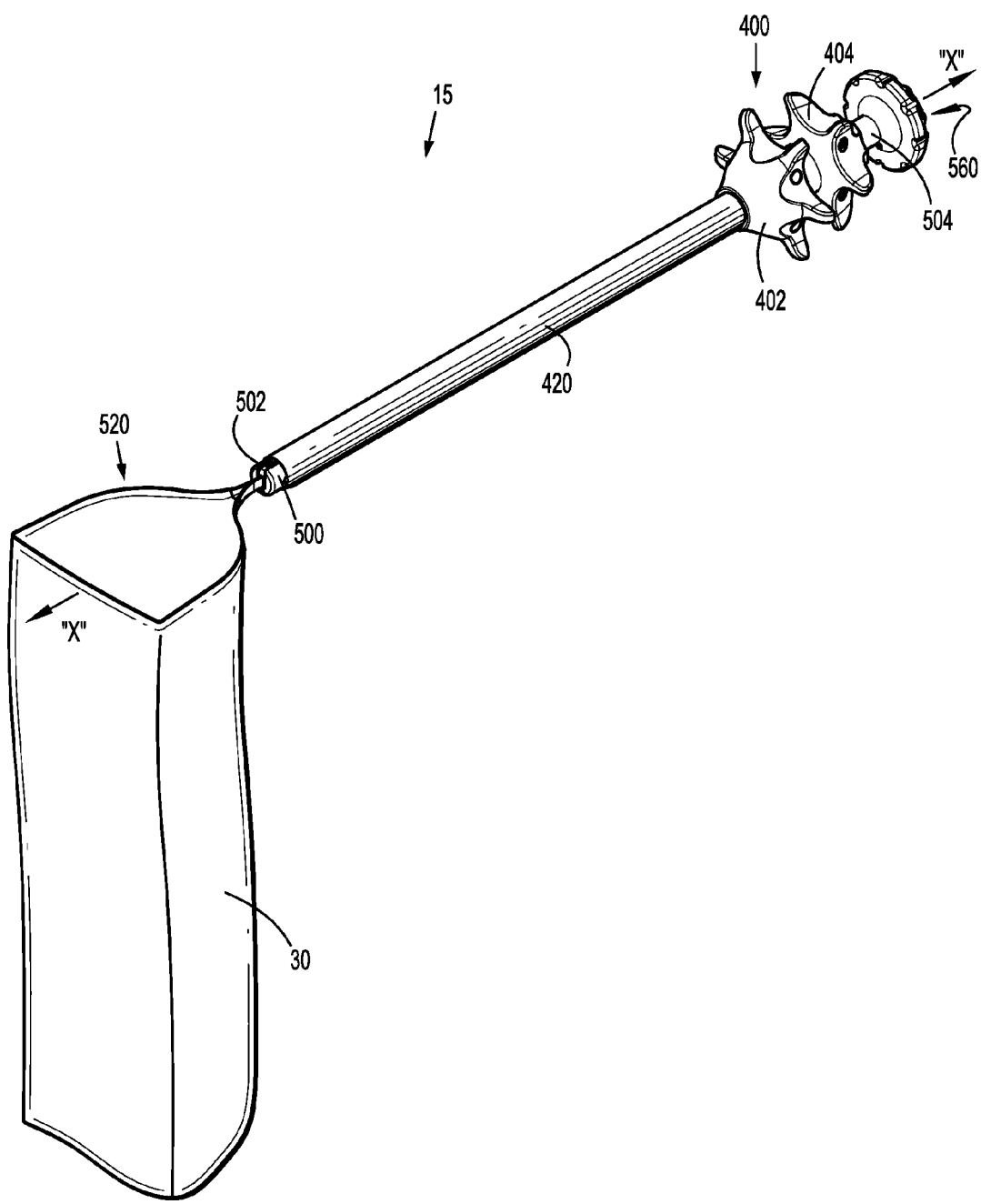
FIG. 35 is a side, perspective view of another embodiment of a surgical retrieval apparatus provided in accordance with the present disclosure.

Turning now to FIGS. 35-37, another embodiment of a surgical retrieval apparatus, similar to surgical retrieval apparatus 10 (FIGS. 1-34), provided in accordance with the present disclosure is shown generally identified by reference numeral 15. Surgical retrieval apparatus 15 generally includes a handle 400 having an elongated sleeve 420 fixedly engaged thereto and extending distally therefrom, a shaft 500 having an end effector assembly 520 disposed at a distal end 502 thereof, an articulation assembly 540 coupled thereto, and a plunger assembly 560 disposed at a proximal end 504 thereof. Surgical retrieval apparatus 15 is substantially similar to surgical retrieval apparatus 10 (FIGS. 1-25) in both configuration and operation, except for the configuration of handle 400 and plunger assembly 560. Thus, only the differences between surgical retrieval apparatus 15 and surgical retrieval apparatus 10 (FIGS. 1-25) will be described in detail hereinbelow to avoid unnecessary repetition.

Handle 400 of surgical retrieval apparatus 15 includes a pair of opposed housing members 402, 404 interconnected by a cylindrical tube 406. Housing members 402, 404 each define a generally-annular configuration having a plurality of flanges 403, 405, respectively, extending radially outwardly therefrom. Flanges 403 are spaced-apart from one another, as are flanges 405, to define a plurality of finger recesses 407 therebetween. Finger recesses 407 facilitate grasping and rotation of handle 400 about longitudinal axis "X-X" relative to shaft 500 in order to articulate end effector assembly 520 and specimen retrieval bag 30 relative to longitudinal axis "X-X." The use and operation of handle 400 is substantially similar to that of handle 100 of surgical retrieval apparatus 10 (FIGS. 1-34).

Plunger 560 of surgical retrieval apparatus 15 is fixedly engaged to proximal end 504 of shaft 500, e.g., via pin 564, and includes a base 561 and a proximal hub 562 extending proximally from base 561. Proximal hub 562 defines a generally-hemispherical configuration wherein the rounded surface 565 thereof faces proximally. Further, proximal hub 562 includes a tab 566 extending from proximal, rounded surface 565 thereof that is configured to releasably retain second end 234 of cinch cord 230 therein. As such, rather than providing a pull-member for securing second end 234 of cinch cord 230 thereto, surgical retrieval apparatus 15 retains second end 234 of cinch cord 230 thereon by engagement within tab 566. Accordingly, when it is desired to retract cinch cord 230 relative to plunger 560 to fully cinch closed specimen retrieval bag 30, second end 234 of cinch cord 230 is disengaged from tab 566 and is translated proximally. The use and operation of surgical retrieval apparatus 15 is otherwise substantially similar to that of surgical retrieval apparatus 10, discussed above with respect to FIGS. 1-34, and, thus will not be repeated here.

Turning now to FIGS. 38-39, another embodiment of a surgical retrieval apparatus 20 provided in accordance with the present disclosure is shown. Surgical retrieval apparatus 20 is substantially similar to similar to surgical retrieval apparatus 15 (FIGS. 35-37) except for the configuration of handle 600. Accordingly, only handle 600 will be described hereinbelow for purposes of brevity.

Handle 600 of surgical retrieval apparatus 20 includes a generally-cylindrical body 602 having a plurality of flanges 604 extending radially outwardly therefrom. Flanges 604 taper distally to proximally and are spaced-apart from one another to define a plurality of finger recesses 606 therebetween that facilitate grasping and rotation of handle 600. Proximal end 608 of handle 600, including the distal ends flanges 604, defines a relatively planar surface extending generally perpendicularly to longitudinal axis "X-X" which may be configured to mate with the planar distal surface 668 of the generally-hemispherical proximal hub 664 of plunger 660. Such a configuration inhibits catching of plunger 660 on the clinician's clothing, interference with other surgical instrumentation, and/or inadvertent movement of shaft 700 relative to handle 600 and elongated sleeve 620.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical retrieval apparatus, comprising:
   a handle defining a longitudinal axis and including an elongated sleeve extending distally therefrom, the handle and the elongated sleeve cooperating to define a lumen extending longitudinally therethrough, the handle defining an articulation track on an inner surface thereof, wherein the articulation track defines a helical configuration;
   a shaft having an end effector assembly disposed at a distal end thereof and a plunger disposed at a proximal end thereof, the shaft selectively translatable between a first position, and a second position, wherein the end effector assembly extends distally from the elongated sleeve;
   an articulation mechanism configured to articulate the end effector assembly relative to the shaft between an aligned position, wherein the end effector assembly is longitudinally aligned relative to the longitudinal axis, and an articulated position, wherein the end effector assembly is disposed at an oblique angle relative to the longitudinal axis, the articulation mechanism including an articulation post configured to move along the articulation track upon rotation of the handle about the longitudinal axis and relative to the shaft to articulate the end effector assembly between the aligned and articulated positions; and
   a specimen retrieval bag coupled to the end effector assembly, the specimen retrieval bag deployable from an undeployed position to an extended position upon movement of the end effector assembly from the first position to the second position.

2. The surgical retrieval apparatus according to claim 1, wherein articulation of the end effector assembly is inhibited when the shaft is disposed in the first position.

3. The specimen retrieval apparatus according to claim 1, wherein the specimen retrieval bag includes a cinch cord disposed about an open end thereof, the cinch cord removably coupled to the plunger at an end thereof, the cinch cord configured, upon release from the plunger, for selective proximal translation to cinch closed the specimen retrieval bag.

4. The surgical retrieval apparatus according to claim 3, further comprising a pull-member releasably coupled to the plunger, the pull-member configured to engage an end of the cinch cord thereon such that, upon release from the plunger, the pull-member is proximally translatable to cinch closed the specimen retrieval bag.

5. The surgical retrieval apparatus according to claim 4, wherein the plunger includes at least one resilient lock tab configured to releasably engage the pull-member thereon.

6. The specimen retrieval apparatus according to claim 1, wherein the articulation mechanism includes an articulation bar coupled to the end effector assembly at a distal end thereof and has the articulation post disposed at a proximal end thereof, the articulation bar disposed within the shaft and translatable relative to the shaft to upon rotation of the handle relative to the shaft to articulate the end effector assembly relative to the shaft.

7. The surgical retrieval apparatus according to claim 1, further comprising a safety tab configured to engage both the handle and the shaft when the shaft is disposed in the first position to inhibit relative movement between the handle and the shaft.

8. The surgical retrieval apparatus according to claim 1, wherein the handle includes at least one finger hole defined therethrough to facilitate manipulation of the handle.

9. The surgical retrieval apparatus according to claim 1, wherein the plunger includes at least one flange extending outwardly therefrom that is configured to facilitate translation of the shaft between the first and second positions.

10. The surgical retrieval apparatus according to claim 1, wherein translation of the shaft from the second position back to the first position separates the specimen retrieval bag from the end effector assembly.

11. The surgical retrieval apparatus according to claim 1, wherein translation of the shaft from the second position back to the first position at least partially cinches closed the specimen retrieval bag.

12. The surgical retrieval apparatus according to claim 1, wherein, in the first position of the shaft, the articulation post is spaced-apart from the articulation track and wherein, in the second position of the shaft, the articulation post is operably coupled with the articulation track.

* * * * *